(12) United States Patent
Hatanaka

(10) Patent No.: US 11,278,273 B2
(45) Date of Patent: Mar. 22, 2022

(54) SUTURE SECURING INSTRUMENT

(71) Applicant: OLYMPUS CORPORATION, Hachioji (JP)

(72) Inventor: Takayuki Hatanaka, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 252 days.

(21) Appl. No.: 16/599,205

(22) Filed: Oct. 11, 2019

(65) Prior Publication Data

US 2020/0038014 A1 Feb. 6, 2020

Related U.S. Application Data

(63) Continuation of application No. PCT/JP2017/015368, filed on Apr. 14, 2017.

(51) Int. Cl.
*A61B 17/04* (2006.01)

(52) U.S. Cl.
CPC ...... *A61B 17/0487* (2013.01); *A61B 17/0467* (2013.01); *A61B 17/0469* (2013.01); *A61B 17/0482* (2013.01); *A61B 2017/0488* (2013.01); *A61B 2017/0496* (2013.01)

(58) Field of Classification Search
CPC ............ A61B 17/0487; A61B 17/0467; A61B 17/0469; A61B 17/0482; A61B 2017/0488; A61B 2017/0496; A61B 2017/045; A61B 2090/037
See application file for complete search history.

(56) References Cited

U.S. PATENT DOCUMENTS

| | | | |
|---|---|---|---|
| 4,473,102 A | 9/1984 | Ohman et al. | |
| 5,376,101 A * | 12/1994 | Green | A61B 17/0487 606/151 |
| 5,584,835 A * | 12/1996 | Greenfield | A61B 17/0401 606/232 |
| 5,899,921 A | 5/1999 | Caspari et al. | |
| 6,592,609 B1 * | 7/2003 | Bonutti | A61B 17/0401 606/232 |

(Continued)

FOREIGN PATENT DOCUMENTS

| | | |
|---|---|---|
| JP | 2001-500778 A | 1/2001 |
| JP | 2010-536486 A | 12/2010 |
| JP | 2012-24276 A | 2/2012 |

OTHER PUBLICATIONS

Oct. 15, 2019 Translation of International Preliminary Report on Patentability issued in International Patent Application No. PCT/JP2017/015368.

(Continued)

*Primary Examiner* — Julian W Woo
(74) *Attorney, Agent, or Firm* — Oliff PLC

(57) ABSTRACT

A suture securing instrument can include a cylindrical body that has an inner circumferential surface, and a securing portion configured to secure a suture. The securing portion can include an outer circumferential surface supported by the inner circumferential surface of the cylindrical body by moving along a longitudinal axis relative to the cylindrical body, and a holding portion configured to hold the suture between the cylindrical body and the securing portion. The holding portion can also include a groove for the suture.

15 Claims, 28 Drawing Sheets

(56) References Cited

U.S. PATENT DOCUMENTS

| | | | |
|---|---|---|---|
| 7,713,286 B2* | 5/2010 | Singhatat | A61B 17/0401 606/232 |
| 11,000,267 B2* | 5/2021 | Hendricksen | B29C 45/00 |
| 2007/0270907 A1 | 11/2007 | Stokes et al. | |
| 2008/0097527 A1* | 4/2008 | Lim | A61B 17/0487 606/232 |
| 2009/0069847 A1 | 3/2009 | Hashiba et al. | |
| 2013/0103080 A1* | 4/2013 | Hernandez | A61B 17/0401 606/232 |

OTHER PUBLICATIONS

Jun. 20, 2017 International Search Report issued in International Patent Application No. PCT/JP2017/015368.
Oct. 13, 2020 Office Action issued in Japanese Patent Application No. 2019-512165.

* cited by examiner

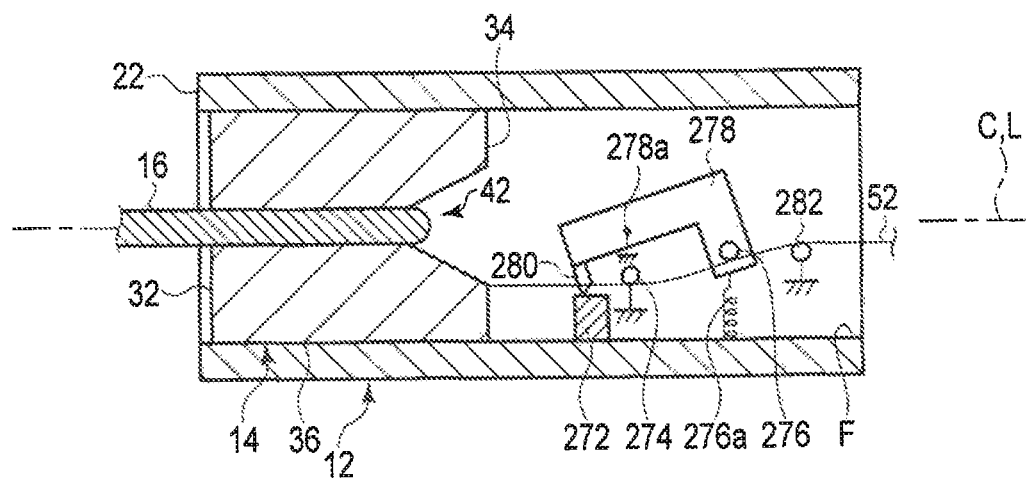
F I G. 15B
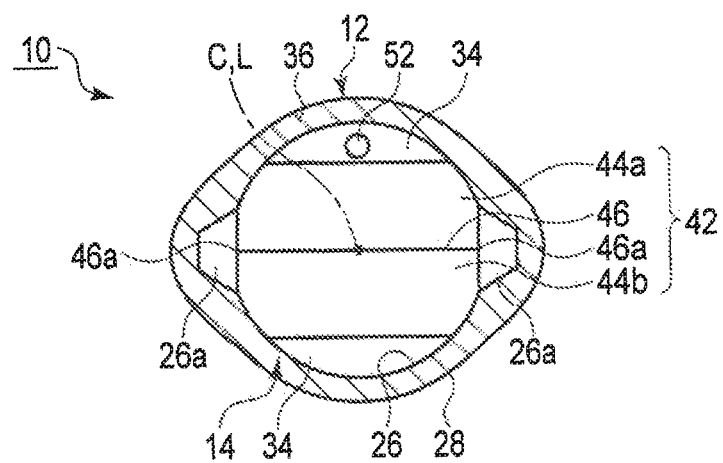
F I G. 16A

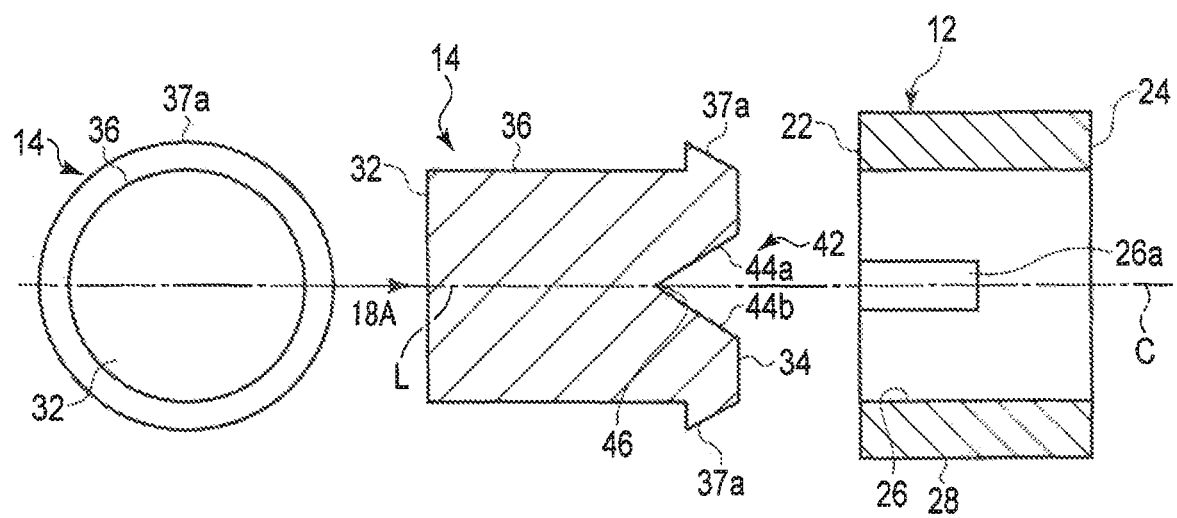
F I G. 18A
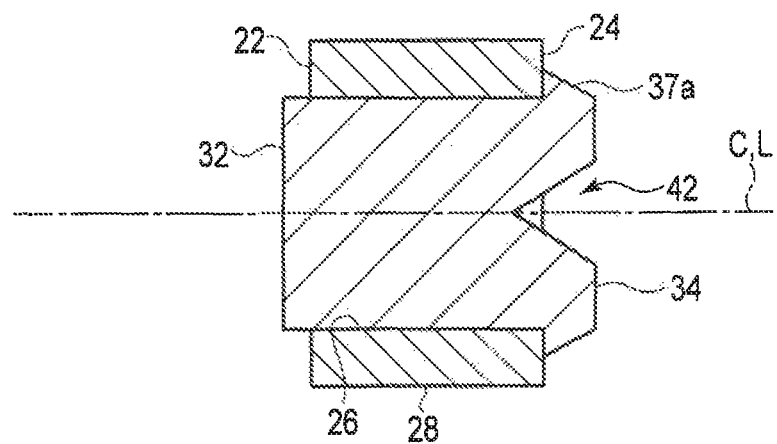
F I G. 18B

SUTURE SECURING INSTRUMENT

CROSS-REFERENCE TO RELATED APPLICATIONS

This application is a Continuation Application of PCT Application No. PCT/JP2017/015368, filed Apr. 14, 2017, the entire contents of which are incorporated herein by reference.

BACKGROUND

For example, US 2007/0270907 A1 discloses a suture securing instrument for securing a suture in treatment. The suture securing instrument has an outer locking member and an inner locking member movable relative to the outer locking member along a longitudinal axis. The distal end of a cable (wire member) is connected to the inner locking member. An inner cavity is formed in the inner locking member. The inner cavity is open to an outside of the inner locking member at a distal end opening of a distal end surface of the inner locking member and at an outer circumferential opening of an outer circumferential surface of the inner locking member. A suture that has sutured a living tissue or the like is inserted from the distal end opening into the inner cavity of the inner locking member, and is extended from the inner cavity to the outside of the inner locking member through the outer circumferential opening. Then, with the suture inserted through the inner cavity, the cable is pulled toward the proximal end side, and the inner locking member is inserted inside the outer locking member. Thus, an extended portion of the suture extended from the outer circumferential opening is sandwiched between the outer circumferential surface of the inner locking member and the inner circumferential surface of the outer locking member. Due to the suture being sandwiched between the inner locking member and the outer locking member, the friction between the suture and the inner locking member and the friction between the suture and the outer locking member lock the suture; thus, the suture is secured to the inner locking member and the outer locking member.

BRIEF SUMMARY

According to an exemplary embodiment, a suture securing instrument that secures a suture, includes: a cylindrical body including an inner circumferential surface extending from one end to another end along a longitudinal axis; and a securing portion extending from a first end to a second end along the longitudinal axis and configured to secure the suture. The securing portion includes an outer circumferential surface supported by the inner circumferential surface of the cylindrical body by moving along the longitudinal axis relative to the cylindrical body; and a holding portion configured to hold the suture, which is interposed between the cylindrical body and the securing portion. The holding portion includes a groove in which the suture is placed from the second end toward the first end, when the suture is held on an end face of the second end so as to intersect the longitudinal axis, the suture is held on the outer circumferential surface of the securing portion, and the securing portion is fitted in the cylindrical body in the direction of the longitudinal axis.

BRIEF DESCRIPTION OF THE SEVERAL VIEWS OF THE DRAWING

The accompanying drawings, which are incorporated in and constituent a part of the specification, illustrate exemplary embodiments and together with the general description given above and the detailed description of the embodiments given below, serve to explain the principles.

FIG. 33 is a schematic cross-sectional view showing the suture securing instrument taken along line 3B-3B in FIG. 3A.

FIG. 15B is a schematic view showing a state in which the wire of the suture securing instrument is cut using the sixth mechanism of the cutting mechanism shown in FIG. 15A, FIG. 16A is a schematic view of a suture securing instrument having an external shape different from that shown in FIG. 1D, showing a cross section of a cylindrical body having a cylindrical inner wall and a cylindrical columnar securing portion.

FIG. 18A is a schematic view showing a cross section of a suture securing instrument in which a cylindrical body having an engaging portion and a securing portion having an engaging portion are separated, which are different from the cylindrical body and the stationary portion of the suture securing instrument shown in FIG. 1A and FIG. 17A, and also showing the securing portion viewed from the direction indicated by an arrow 18A.

FIG. 18B is a schematic view showing a cross section of the suture securing instrument shown in FIG. 18A in which the engagement portions of the cylindrical body and the securing portion are engaged.

DETAILED DESCRIPTION

Figure 1A:
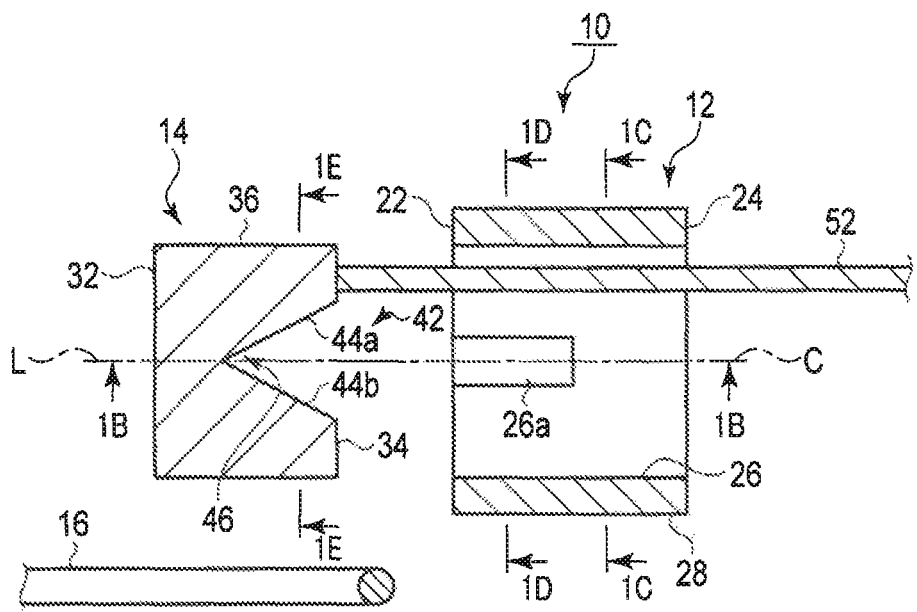
FIG. 1A is a schematic cross-sectional view showing a suture securing instrument according to an exemplary embodiment, in which a cylindrical body and a securing portion are separated, and a suture is secured to the suture securing instrument.

Hereinafter, exemplary embodiments will be described with reference to the accompanying drawings.

The suture securing instrument (suture locking tool) 10 according to an exemplary embodiment will be described with reference to FIG. 1A to FIG. 7.

As shown in FIG. 1A to FIG. 1E, the suture securing instrument 10 includes a cylindrical body 12 and a securing portion (holding portion) 14. As a suture 16, an appropriate one is used in accordance with the tissue of a living body such as a human body or an animal. It preferable to use the suture 16 that has an appropriate strength and appropriate stiffness. As will be described later, when the securing portion 14 is supported by the cylindrical body 12 in a state where the suture 16 located in a predetermined positional relationship with the securing portion 14, the cylindrical body 12 and the securing portion 14 maintain a supported state and maintain a state of securing the suture 16.

It is preferable that the cylindrical body 12 and the securing portion 14 be formed of a known metal material or resin materiel having biocompatibility. The cylindrical body 12 and the securing portion 14 may both be formed a metal material, and may both be formed of a resin material. If the cylindrical body 12 is formed of a metal material, the securing portion 14 may be formed of a resin material. If the cylindrical body 12 is formed resin material, the securing portion 14 may be formed of a metal material.

The cylindrical body 12 has a one end (distal end) 22 and another end (proximal end) 24. The cylindrical body 12 includes an inner circumferential surface (inner wall surface) 26 and an outer circumferential surface (outer wall surface) 28 between the one end 22 and the other end 24. A central axis C of the cylindrical body 12 (a centroid axis which is an aggregate of the positions of the center of gravity of the cross sections between the one end 22 and the other end 24) is defined based on the shape of the inner circumferential surface 26 between the one end 22 and the other end 24.

Figure 1B:
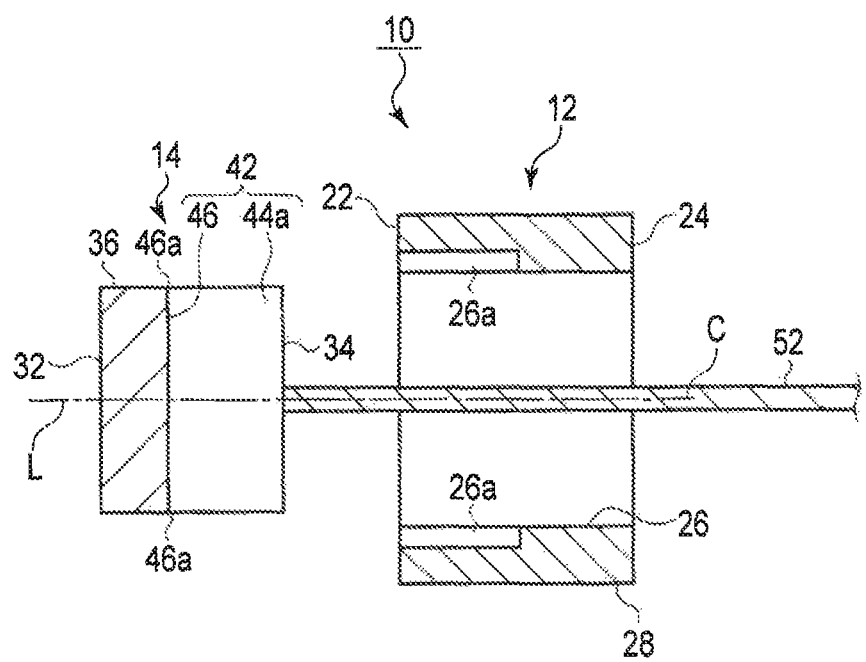
FIG. 1B is a schematic cross-sectional view showing the suture securing instrument taken along line 1B-1B in FIG. 1A.
Figure 1C:
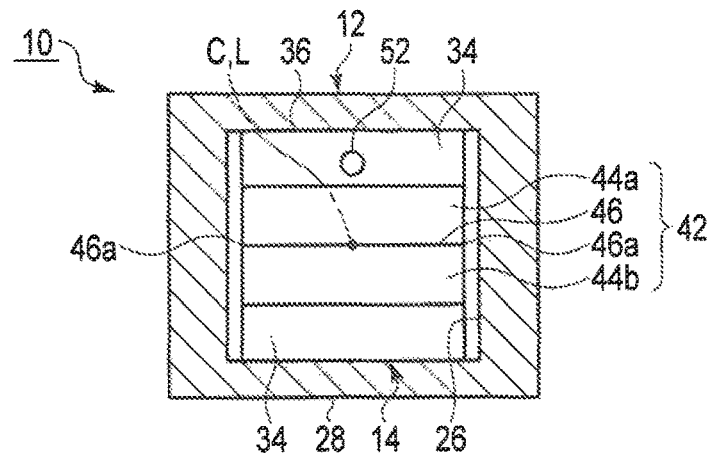
FIG. 1C is a schematic view showing a cross section of the cylindrical body of the suture securing instrument taken along line 1C-1C in FIG. 1A and a securing portion of the suture securing instrument.
Figure 1D:
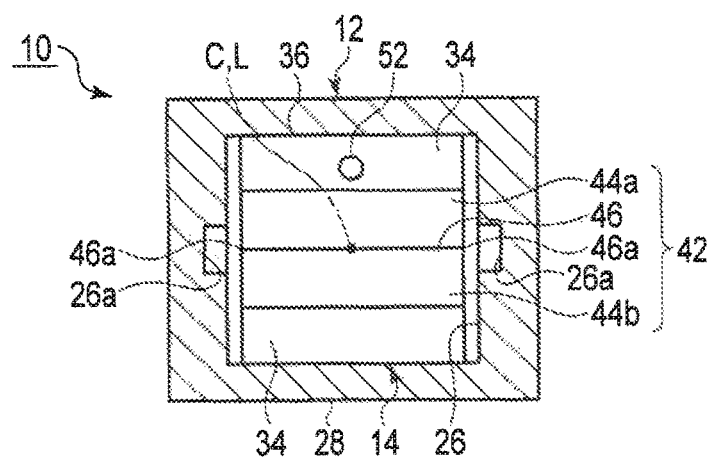
FIG. 1D is a schematic view showing a cross section of the cylindrical body of the suture securing instrument along line 1D-1D in FIG. 1A and the securing portion of the suture securing instrument.
Figure 1E:
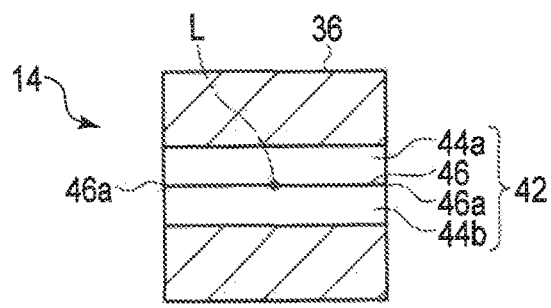
FIG. 1E is a schematic view showing a cross section of the securing portion of the suture securing instrument taken along line 1E-1E in FIG. 1A.

In the present embodiment, as shown in FIG. 1C and FIG. 1D, the cross section of the inner circumferential surface 6 orthogonal to the central axis C of the cylindrical body 12 is formed in a substantially rectangular shape. As shown in FIG. 1A, FIG. 1B and FIG. 1D, the inner circumferential surface 26 includes a pair of concave grooves (suture locking grooves) 26a parallel to the central axis C to locate the suture 16 between the inner circumferential surface and an outer circumferential surface 36 (described later) of the securing portion 14. It is preferable that the concave grooves 26a face each other with respect to the central axis C. The concave grooves 26a are formed from one end 22 toward the other end 24. The circumferential width around the central axis C of the concave groove 26 a can be set as appropriate, but is preferably larger than the diameter of the suture 16. As shown in FIG. 1C, the concave groove 26a may not be formed at the other end 24. In addition, the inner circumferential surface 26 of the cylindrical body 12 and the outer circumferential surface 36 of the securing portion 14 are spaced apart, in such a state that the suture 16 can be locked or held with light force by the concave grooves 26a. The gap between the inner circumferential surface 26 of the cylindrical body 12 and the outer circumferential surface 36 of the securing portion 14 may suffice as long as the path of the suture 16 is restricted to a desired state, and need not fix the suture 16.

As shown in FIG. 1A to FIG. 1E, the securing portion 14 is formed in a block shape or columnar shape. The securing portion 14 may be formed in a cylindrical shape. In the present embodiment, the securing portion 14 is formed a square pole. The securing portion 14 includes a first end (end face) 32, a second end (end face) 34, and an outer circumferential surface 36, at least a part of the outer circumferential surface between the first end 32 and the second end 34 being supported by the inner circumferential surface 26 of the cylindrical body 12. A longitudinal axis L of the securing portion 14 is defined by the first end 32 and the second end 34. More specifically, a longitudinal axis (a centroid axis which is an aggregate of the positions of the center of gravity of the cross sections between the first end 32 and the second end 34) L is defined based on the shape of the outer circumferential surface 36 between the first end 32 and the second end 34.

In the present embodiment, each of the first end 32 and the second end 34 is formed as a plane orthogonal to the longitudinal axis L, for example, Each of the first end 32 and the second end 34 may adopt an appropriate shape such as a convex curved surface or a concave curved surface.

The securing portion 14 includes a holding portion (locking groove) 42 configured to hold the suture 16 for use in surgical treatment at a position continuous with the second end 34 of the securing portion 14. The holding portion 42 includes a pair of guides 44a and 44b and a bottom portion 46 between the guides 44a and 44b. The holding portion 42 is formed in a substantially V-shape in which the pair of guides 44a and 44b and the bottom portion 46 are continuous. For this reason, the bottom portion 46 of the holding portion 42 is formed in a substantially V-shape continuous with the guides 44a and 44b. The guides 44a and 44b are at positions facing each other. In FIGS. 1A and 1B, the guides 44a and 44b are each formed as a plane, but may be a curved surface. In the present embodiment, the bottom portion 46 extends in a direction perpendicular to the longitudinal axis L. The bottom portion 46 is formed between a pair of end portions 46a continuous with the outer circumferential surface of the securing portion 14. The pair of end portions 46a of the bottom portion 46 face the concave grooves 26a of the inner circumferential surface 26 of the cylindrical body 12 when the securing portion 14 is supported by the cylindrical body 12.

Figure 5A:
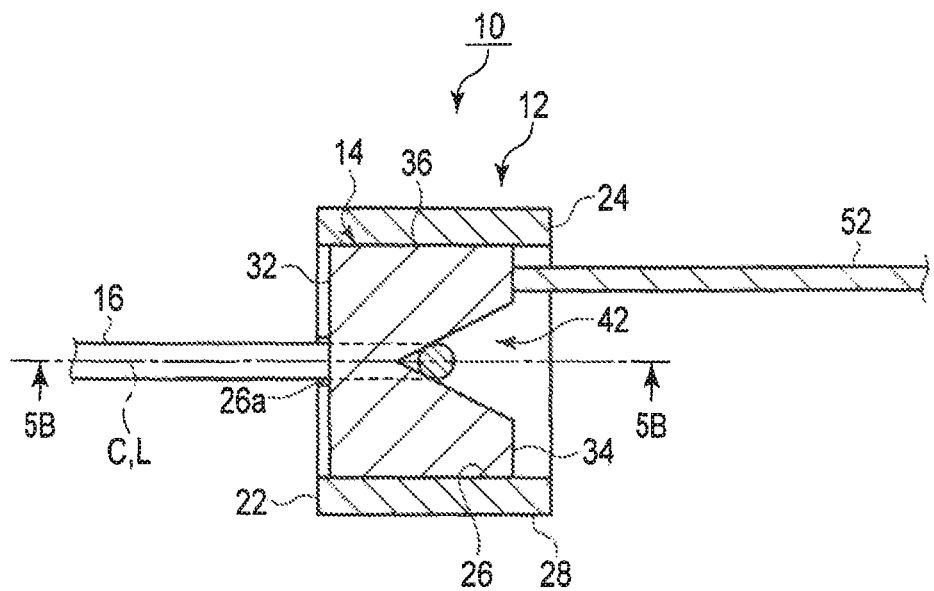
FIG. 5A is a schematic cross-sectional view showing a state in which the securing portion of the suture securing instrument shown in FIG. 4A is further moved toward the other end of the cylindrical body, so that the suture is located between the groove of the cylindrical body and the outer circumferential surface of the securing portion and held on the bottom portion of the holding portion of the securing portion, thereby securing the suture to the suture securing instrument.
Figure 5B:
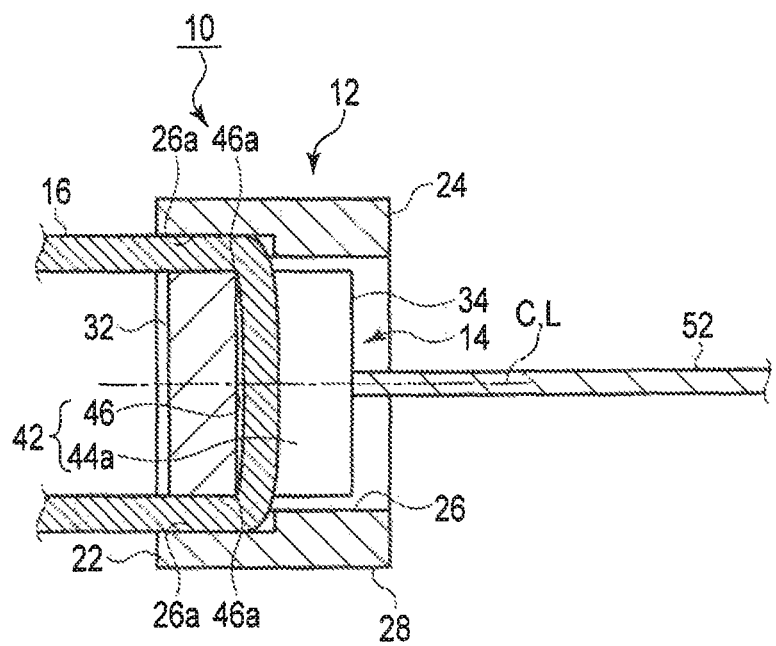
FIG. 5B is a schematic cross-sectional view showing the suture securing instrument taken along line 5B-5B in FIG. 5A.
Figure 5C:
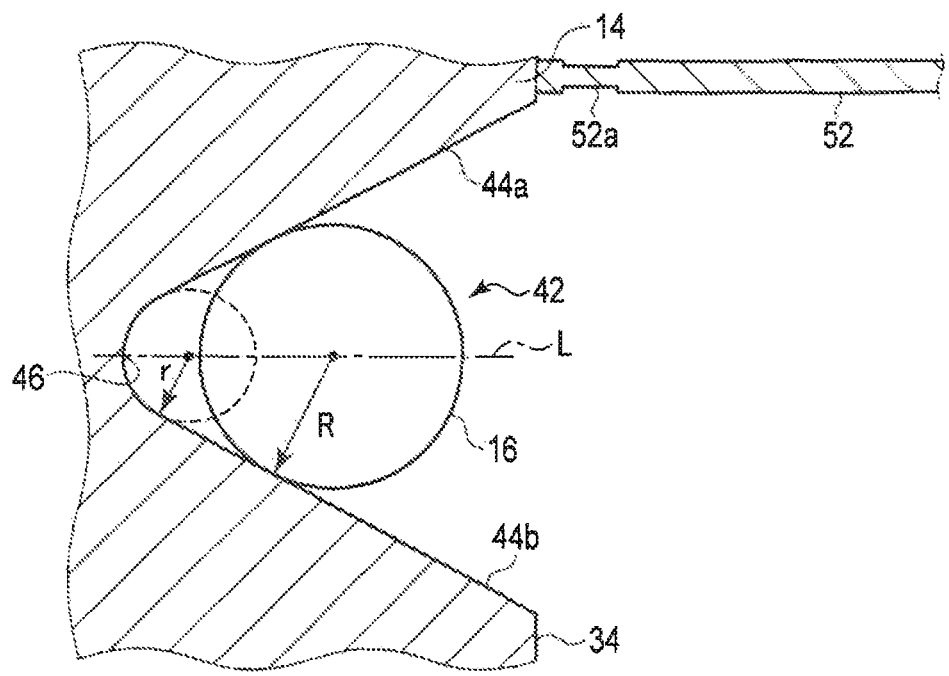
FIG. 5C is a schematic enlarged cross-sectional view showing the holding portion holding a suture and showing the wire in the securing portion of the suture securing instrument in FIG. 5A.

As shown in an enlarged view of FIG. 5C, the bottom portion 46 of the holding portion 42 is formed as a suitable curved surface, for example. The bottom portion 46 of the holding portion 42 is formed, for example, as a part of a circular arc. The radius r of the bottom portion 46 of the holding portion 42 is smaller than the radius R of the suture 16. For this reason, as will be detailed later, when the suture 16 moves toward the bottom portion 46 of the holding portion 42 while tension is applied to the suture 16, the suture 16 is firmly locked and held by the bottom portion 46 and the guides 44a and 44b in the vicinity thereof. Therefore, the holding portion 42 allows the suture 16 to be forced toward and secured to the bottom portion 46.

The angle between the guides 44a and 44b defined by the bottom portion 46 may be any angle as long as the holding portion 42 can hold the suture 16 between the guides 44a and 44b. Therefore, the angle between the guides 44a and 44b is appropriately set in accordance with, for example, the radius R of the suture 16 used for treatment. The distance between the guides 44a and 44b at a position close to the second end 34 is greater than the diameter (2R) of the suture 16 to be secured. Thus, the suture 16 is movable from the second end 34 toward the bottom portion 46 of the holding portion 42.

The radius r of the bottom portion 46 of the holding portion 42 and the radius P. of the suture 16 varies, according to the kind of suture 16; for example, they are smaller than 1 mm, about 1 mm, etc.

As shown in FIGS. 1A and 1B, one end of a wire 52 is fixed to the second end 34 of the securing portion 14. The wire 52 passes through the inside of the cylindrical body 12. Although not shown, the outside of the wire 52 may be covered with a tube or sheath. The tube or sheath covering the wire 52 may be soft as a flexible body or hard as a rigid body.

When the wire 52 is pulled from the securing portion 14 while maintaining the position of the securing portion 14 and receives an appropriate tension (traction force), the wire 52 is broken. As will be detailed later, the wire 52 is required to not break until the suture 16 is properly secured or locked to the cylindrical body 12 and the securing portion 14 (see FIGS. 5A and 5B). For this reason, the breaking strength of the wire 52 is larger than the force necessary to pull the wire 52 to support on the cylindrical body 12 the securing portion 14, in which the suture 16 is locked. The broken position of the wire 52 is preferably as close to the securing portion 14 as possible. For example, as shown in FIG. 5C, the wire 52 has a small diameter portion (breakable portion) 52a that has a diameter smaller than a normal diameter and that allows a break by tension. The small diameter portion 52a is formed to have an appropriate length, and causes a greater stress concentration compared to other portions when a tension is applied to the wire 52.

The wire 52 can be cut at an appropriate position with a suitable cutting tool (not shown) such as scissors. The wire 52 of the suture securing instrument 10 can also be cut using a cutting mechanism 210 (see FIGS. 10 to 15B) described later.

Figure 7:
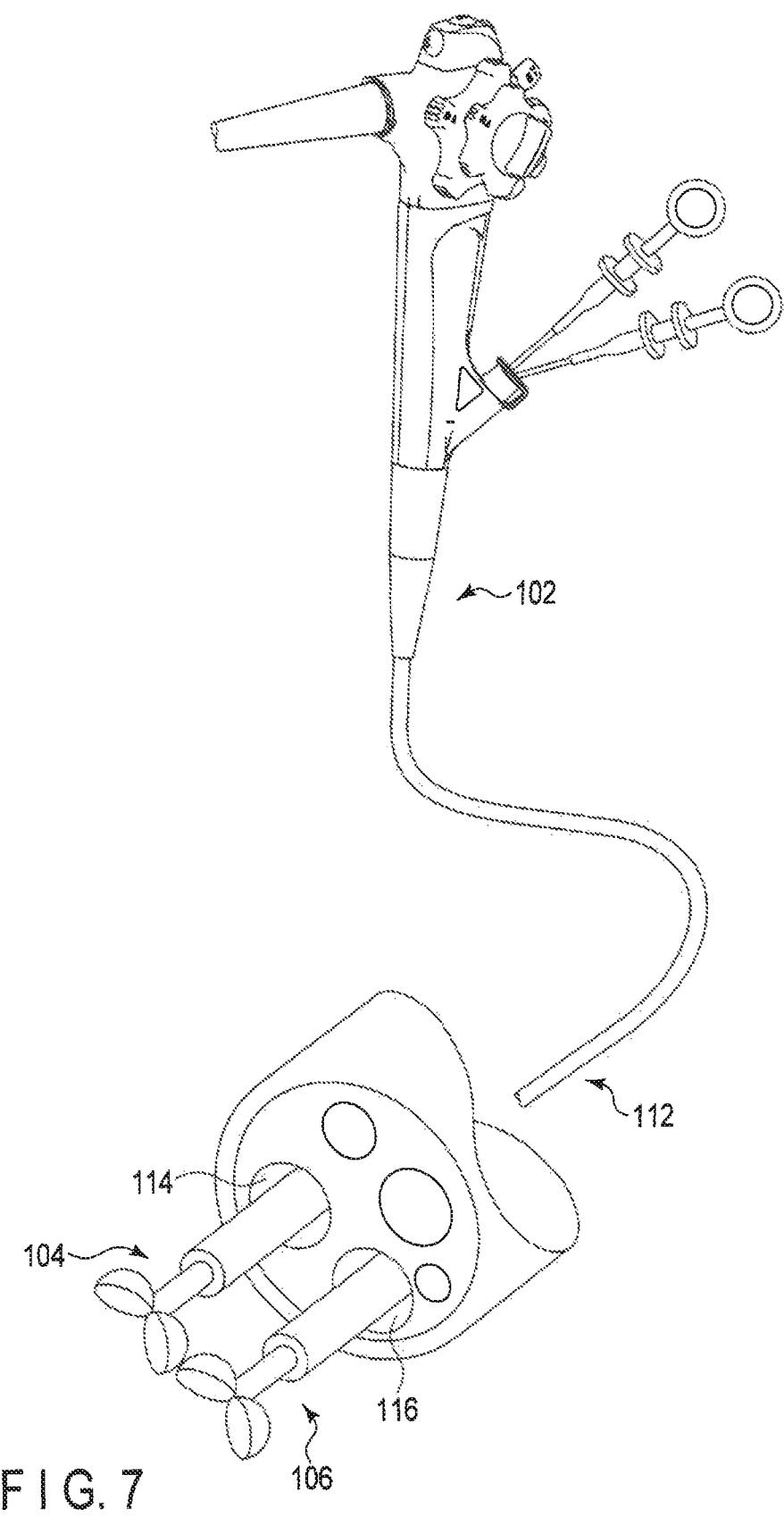
FIG. 7 is a schematic diagram showing an endoscope and grasping forceps respectively inserted through two insertion channels of the endoscope, which are used when inserting the suture securing instrument according to an exemplary embodiment into a body, and when pulling the wire of the suture securing instrument.

Next, operations of the suture securing instrument 10 according to this embodiment will be described. Here, an example using an endoscope 102 and forceps (grasping forceps) 104 and 106 shown in FIG. 7 will be described, but in the case of open abdominal surgery and the like, the endoscope 102 may be unnecessary. The endoscope 102 shown in FIG. 7 is a so-called flexible endoscope having a flexible insertion portion 112. However, depending on surgery positions, the insertion portion 112 may be preferably formed of a rigid body, such as a metal material.

As shown in FIGS. 1A and 1B, the wire 52 connected to the securing portion 14 of the suture securing instrument 10 is inserted into the inside of the cylindrical body 12. In this state, the cylindrical body 12 and the securing portion 14 of the suture securing instrument 10 is inserted into the body through at leapt one of treatment instrument insertion channels 114 and 116 of the insertion portion 112 of the endoscope 102, for example, using the grasping forceps 104 and 106. Then, the suture 16 to be secured by the suture securing instrument 10 is disposed in the vicinity of the securing portion 14.

Figure 2A:
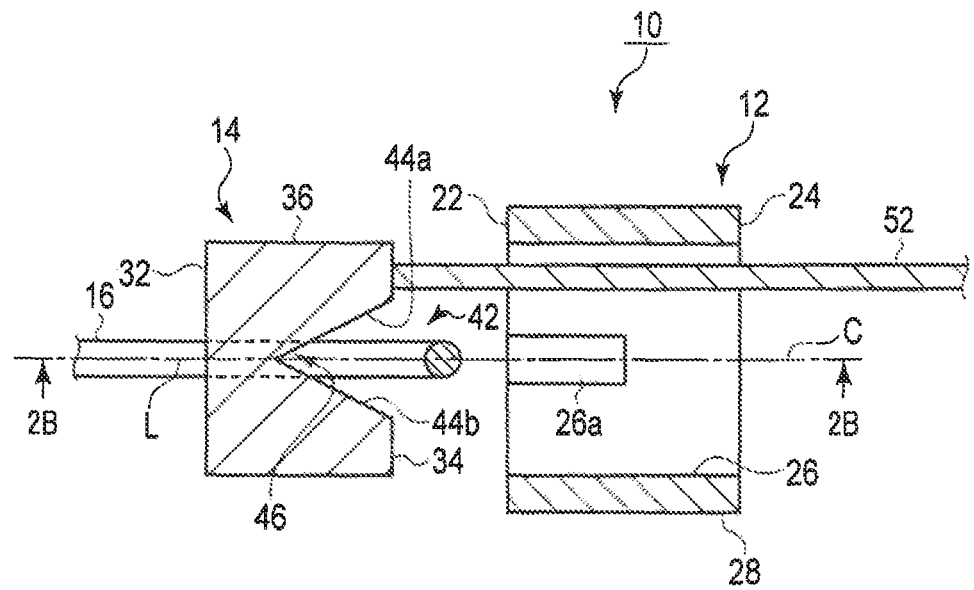
FIG. 2A is a schematic cross-sectional view showing a state in which a suture is placed to face a holding portion of a securing portion of the suture securing instrument shown in FIG. 1A in a direction orthogonal to a longitudinal axis of the securing portion.
Figure 2B:
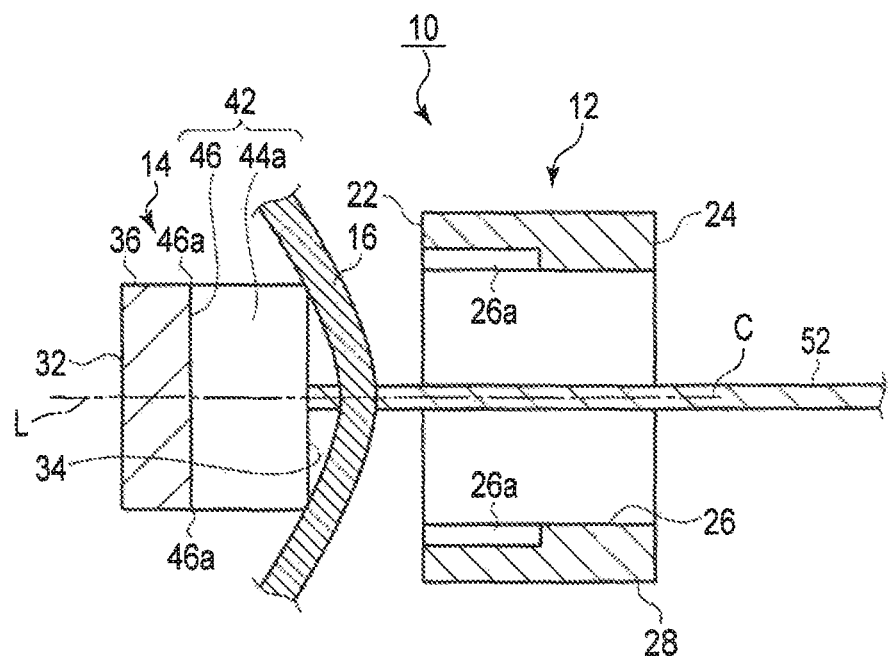
FIG. 2B is a schematic cross-sectional view showing the suture securing instrument taken along line 2B-2B in FIG. 2A.

As shown in FIGS. 2A and 2B, for example, the grasping forceps 104 and 106 are used to relatively move the suture 16 and the securing portion 14 to move the suture 16 from a position deviated from the longitudinal axis L to a position orthogonal to the longitudinal axis L. At this time, the suture 16 is caused to face the holding portion 42 of the securing portion 14.

Figure 3A:
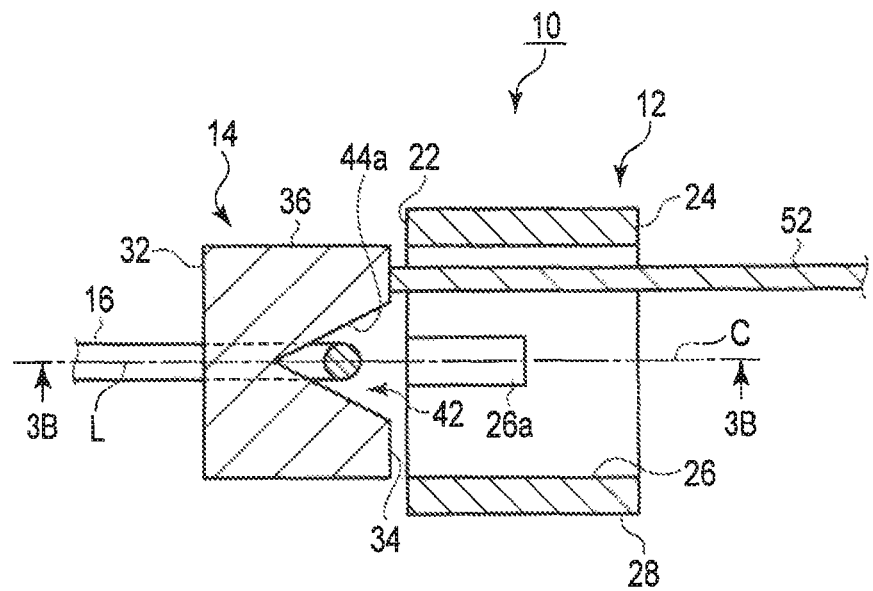
FIG. 3A is a schematic cross-sectional view showing a state in which the suture is guided to a bottom portion of the holding portion of the securing portion, while the securing portion of the suture securing instrument shown in FIG. 2A is being brought close to one end of the cylindrical body.
Figure 3B:
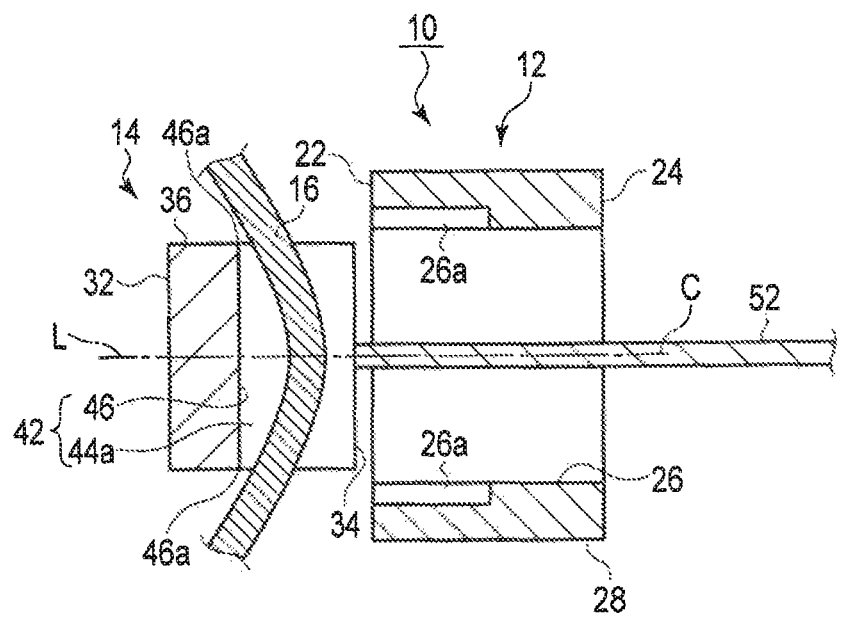

When the wire 52 is pulled toward the cylindrical body 12 using the grasping forceps 104 and 106, the securing portion 14 moves along the longitudinal axis L with respect to the cylindrical body 12 as shown in FIGS. 3A and 3B. Therefore, the second end 34 of the securing portion 14 approaches the one end 22 of the cylindrical body 12.

The diameter (2R) of the suture 16 is smaller than the distance at the second end 34 between the guides 44a and 44b of the holding portion 42 of the securing portion 14. Therefore, when the wire 52 is pulled toward the cylindrical body 12 using the grasping forceps 104 and 106, the suture 16 is guided between the guides 44a and 44b of the holding portion 42 as shown in FIGS. 3A and 3B. The suture 16 is pulled toward the bottom portion 46 of the holding portion 42. The suture 16 is guided towards the bottom portion 46 in response to the pulling of the wire 52. The suture 16 is guided from the direction intersecting the longitudinal axis L toward the bottom portion 46 by the pair of guides 44a and 44b of the holding portion 42 of the securing portion 14.

Figure 4A:
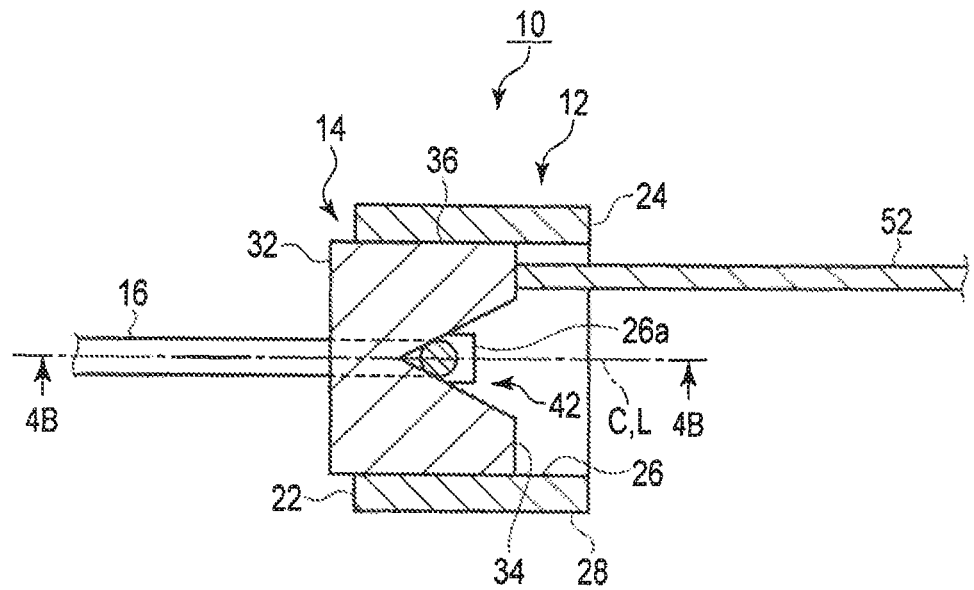
FIG. 4A is a schematic cross-sectional view showing a state in which the suture is guided to the bottom portion of the holding portion of the securing portion and guided to a part between a groove of the cylindrical body and the outer circumferential surface of the securing portion, while the wire is being pulled to move the securing portion of the suture securing instrument shown in FIG. 3A from one end of the cylindrical body to the other end.
Figure 4B:
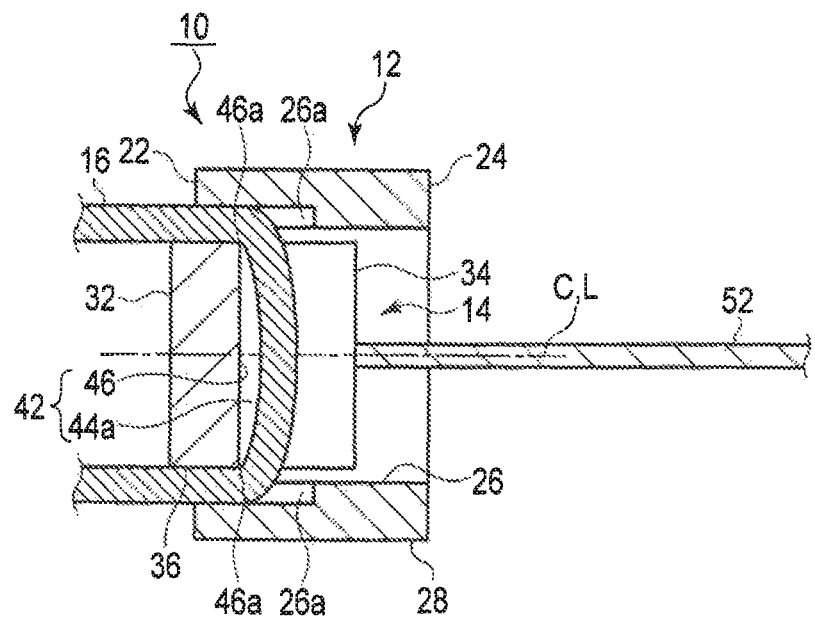
FIG. 4B is a schematic cross-sectional view showing the suture securing instrument taken along line 4B-4B in FIG. 4A.

When the wire 52 is further pulled toward the cylindrical body 12 using the holding forceps 104 and 106, as shown in FIGS. 4A and 4B, the second end 34 of the securing portion 14 is inserted into the one end 22 of the cylindrical body 12. Thus, the second end 34 of the securing portion 14 is moved along the inner circumferential surface 26 of the cylindrical body 12 through the one end 22 of the cylindrical body 12 toward the other end 24. At this time, the suture 16 is guided toward the bottom portion 46 by the guides 44a and 44b of the holding portion 42 while the suture 16 is bent at the ends 46a of the bottom portion 46 of the holding portion 42. The suture 16 protrudes from the end 22 of the cylindrical body 12. As the degree of insertion of the securing portion 14 into the cylindrical body 12 increases, the suture 16 is bent and caught between the outer circumferential surface 36 of the securing portion 14 and the concave groove 26a of the inner circumferential surface 26 of the cylindrical body 12 and locked with a light force (without a high stress on the suture 16). At this time, it is preferable that the central axis C of the cylindrical body 12 and the longitudinal axis L of the securing portion 14 coincide with each other.

The grasping forceps 104 and 106 are used to further pull the wire 52 into the cylindrical body 12. The lock of the suture 16 between the outer circumferential surface 36 of the securing portion 14 and the concave groove 26a the inner circumferential surface 26 of the cylindrical body 12 suppresses the suture 16 from moving toward the other end 24 of the cylindrical body 12. Therefore, as shown in FIGS. 5A and 5B, the suture 16 is guided toward the bottom portion 46 by the guides 44a and 44b of the holding portion 42. At this time, since the suture 16 between the outer circumferential surface 36 of the securing portion 14 and the concave groove 26a of the inner circumferential surface 26 of the cylindrical body 12 is locked, tension is gradually applied to the suture 16 the holding portion 42. Thus, the securing portion 14 applies tension to the suture 16 by the holding portion 42 in cooperation with the cylindrical body 12 in a state where the suture 16 is locked to the holding portion 42. The cylindrical body 12 urges the suture 16 toward the bottom portion 46 of the holding portion 42 so that the suture 16 is folded back at the securing portion 14. Therefore, the suture 16 is moved toward the bottom portion 46 between the guides 44a and 44b, and locked and held.

As described above, the outer circumferential surface 36 of the securing portion 14 is fitted to and supported on the inner circumferential surface 26 of the cylindrical body 12 by moving the securing portion 14 along the longitudinal axis L with respect to the cylindrical body 12, in a state where the suture 16 is disposed in the holding portion 42 of the securing portion 14. In this case, the suture 16 is locked between the inner circumferential surface 26 of the cylindrical body 12 and the outer circumferential surface 36 of the securing portion 14. Furthermore, the suture 16 is held by the holding portion 42 to secure the suture 16 on the cylindrical body 12. At this time, the suture 16 is substantially U-shaped in the suture securing instrument 10.

When the cylindrical body 12 and the securing portion 14 of the suture breaking device 10 are thus fitted and supported, and the suture 16 is held by the holding portion 42, the securing portion 14 is, for example, relatively press-fitted in the cylindrical body 12. In this case, the friction between the inner circumferential surface 26 of the cylindrical body 12 and the outer circumferential surface 36 of the securing portion 14 prevents the securing portion 14 from being unintentionally detached from the cylindrical body 12.

As shown in FIG. 5C, the distance between the guides 44a and 44b of the holding portion 42 decreases toward the bottom portion 46. For this reason, while tension is applied to the suture 16, the suture 16 moves toward the bottom portion 46 of the holding portion 42, the suture 16 is firmly held by the bottom portion 46 and the guides 44a and 44b in the vicinity thereof.

Tension is applied to the wire 52, for example, by pulling by the forceps 104. As described above, in a state where the securing portion 14 is supported on the cylindrical body 12 and the suture 16 is firmly secured to the suture securing instrument 10, the breakable portion 52a of the wire 52 has an allowable range of resistance against tension.

When the securing portion 14 is supported on the cylindrical body 12, as the tension on the suture 16 increases, the suture 16 is more strongly attracted to the holding portion 42 of the securing portion 14. For this reason, the suture 16 is secured to the suture securing instrument 10 with a sufficient amount of force.

Figure 6A:
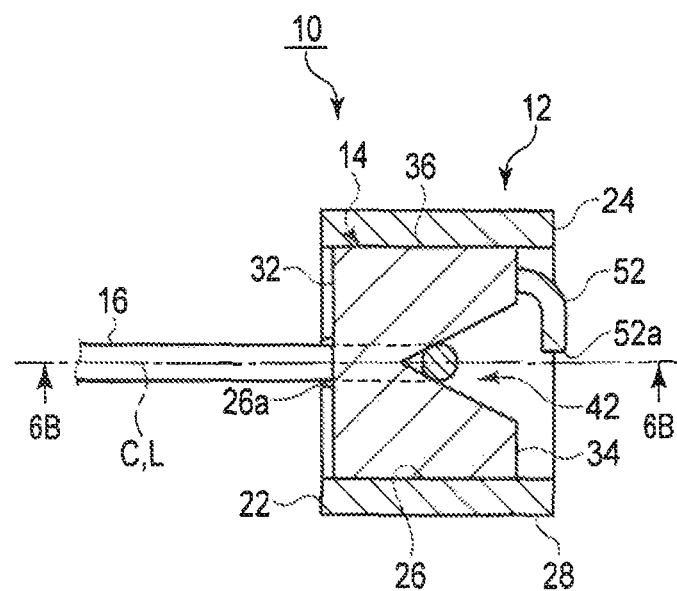
FIG. 6A is a schematic cross-sectional view showing a state in which the wire of the suture securing instrument shown in FIG. 5A is cut.
Figure 6B:
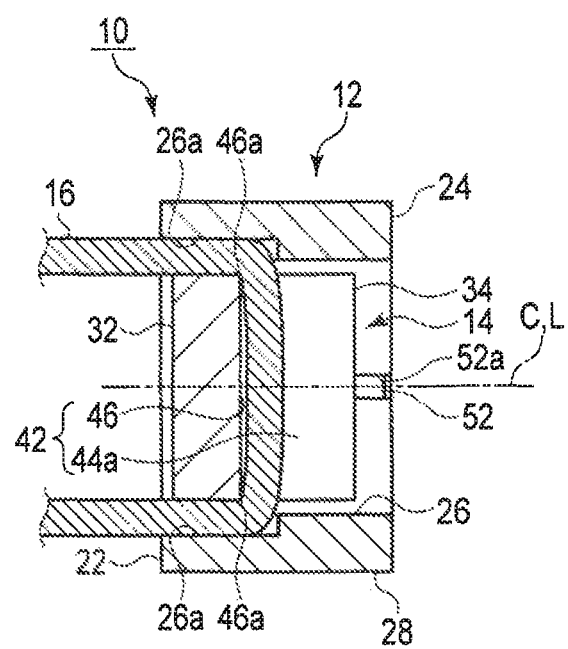
FIG. 6B is a schematic cross-sectional view showing the suture securing instrument taken along line 6B-6B in FIG. 6A.

Next, the wire 52 is broken or cut, as shown in FIGS. 6A and 6B.

First, the case where the wire 52 is broken will be described. While the position of the suture securing instrument 10, to which the suture 16 is secured, is maintained by the grasping forceps 106, the wire 52 is further pulled with the grasping forceps 104. When a tension exceeding the resistance of the small diameter portion 52a is applied, the wire 52 breaks at the small diameter portion 52a. Thus, the wire 52 is broken when the tension applied to the wire 52 exceeds a predetermined value due to the pulling by the grasping forceps 104.

Even when the tension that can break the wire 52 is applied to the small diameter portion a, the friction between the inner circumferential surface 26 of the cylindrical body 12 and the outer circumferential surface 36 of the securing portion 14 suppresses the outer circumferential surface 36 of the securing portion 14 from moving relative to the inner circumferential surface 26 of the cylindrical body along the central axis C (longitudinal axis L). For this reason, an excessive load is suppressed from being applied to the suture 16 disposed and locked in the gap (concave groove 26a) between the inner circumferential surface 26 of the cylindrical body 12 and the outer circumferential surface 36 of the securing portion 14.

On the other hand, in the case of cutting the wire 52, for example, the grasping forceps 106 is removed from the channel 116 of the endoscope 102, and a forceps (not shown) for cutting the wire 52 is inserted into the channel 116. While the wire 52 is held by the forceps 104, an appropriate position of the wire 52 is cut by the working portion of the forceps (not shown). Known forceps may be used as the forceps for cutting the wire 52.

Figure 8A:
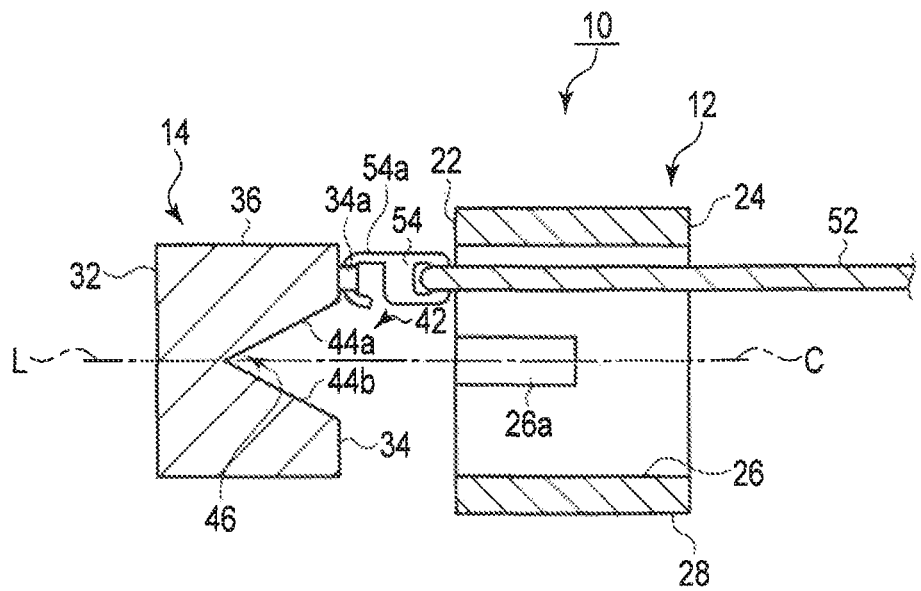
FIG. 8A is a schematic view showing a modification of a connection structure between the securing portion and the wire of the suture securing instrument.
Figure 8B:
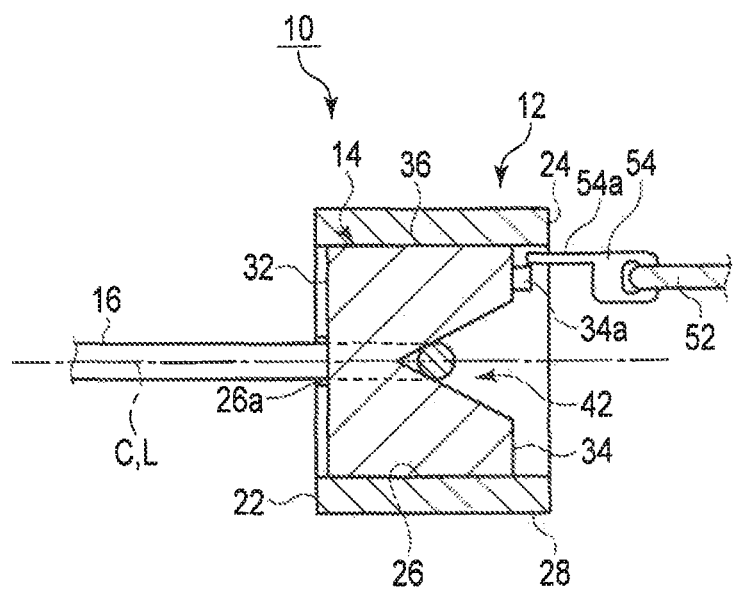
FIG. 8B is a schematic view showing a state in which the connection state of the wire is released with respect to the securing portion of the suture securing instrument shown in FIG. 8A.

An example shown in FIGS. 8A and 8B is also preferable as the connection between the securing portion 14 and the wire 52.

For example, a ring-shaped or substantially C-shaped support portion 34a is formed at the end portion 34 of the securing portion 14. The support portion 34a protrudes from the end portion 34 toward the proximal end side along the longitudinal axis L in this example, but may be formed flush with the end portion 4. A connection member 54 is connected to the distal end of the wire 52. The connection member 54 includes a hook 54a, which is supported by the support portion 34a of the securing portion 14. The hook 54a deforms from the state shown in FIG. 8A to the state shown in FIG. 8B when the wire 52 is pulled by a predetermined force. That is, in the same state as shown in FIGS. 5A and 5B in which the suture 16 is appropriately secured or locked to the cylindrical body 12 and the securing portion 14, the hook 54a deforms from the state shown in FIG. 8A to the state shown in FIG. 8B. Thus, the connection between the securing portion 14 on one hand and the wire 52 and the connection member 54 on the other is released.

Figure 9A:
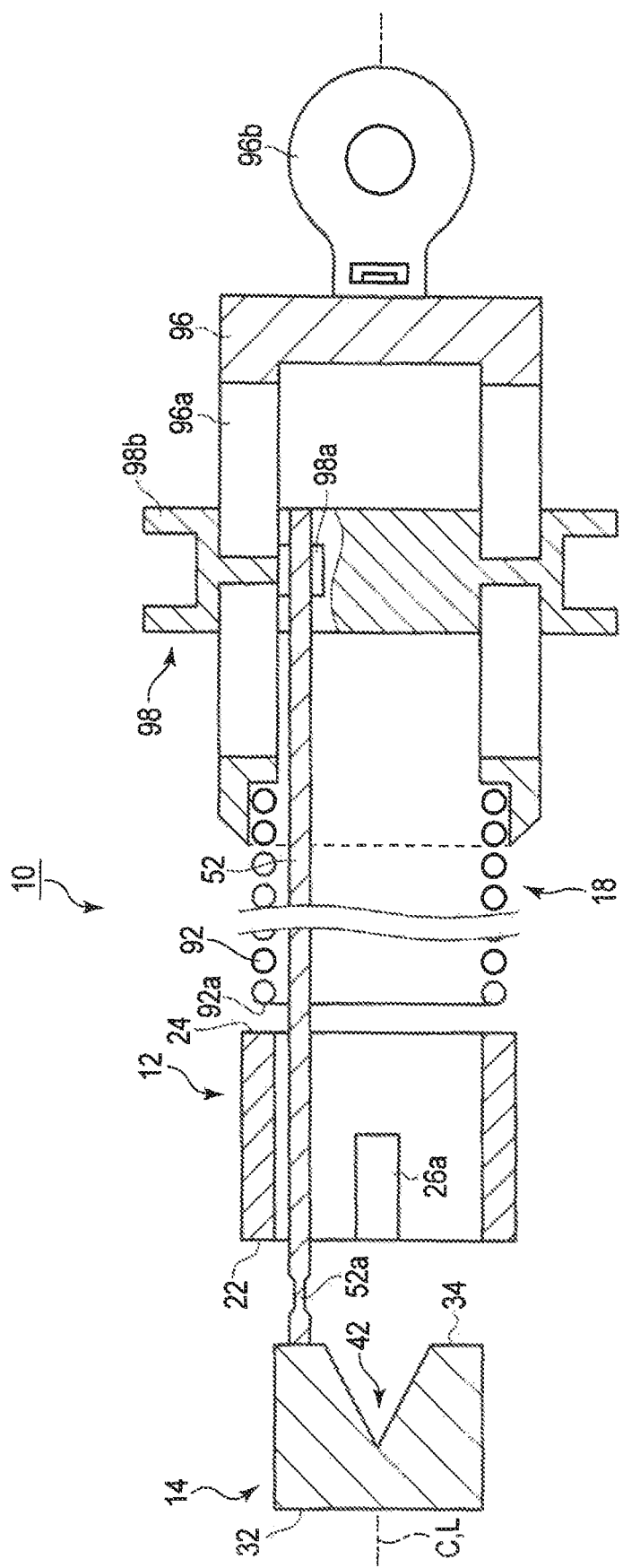
FIG. 9A is a schematic cross-sectional view showing the cylindrical body and the securing portion of the suture securing instrument, and an applicator of the suture securing instrument for introducing the cylindrical body and the securing portion into a body cavity.
Figure 9B:
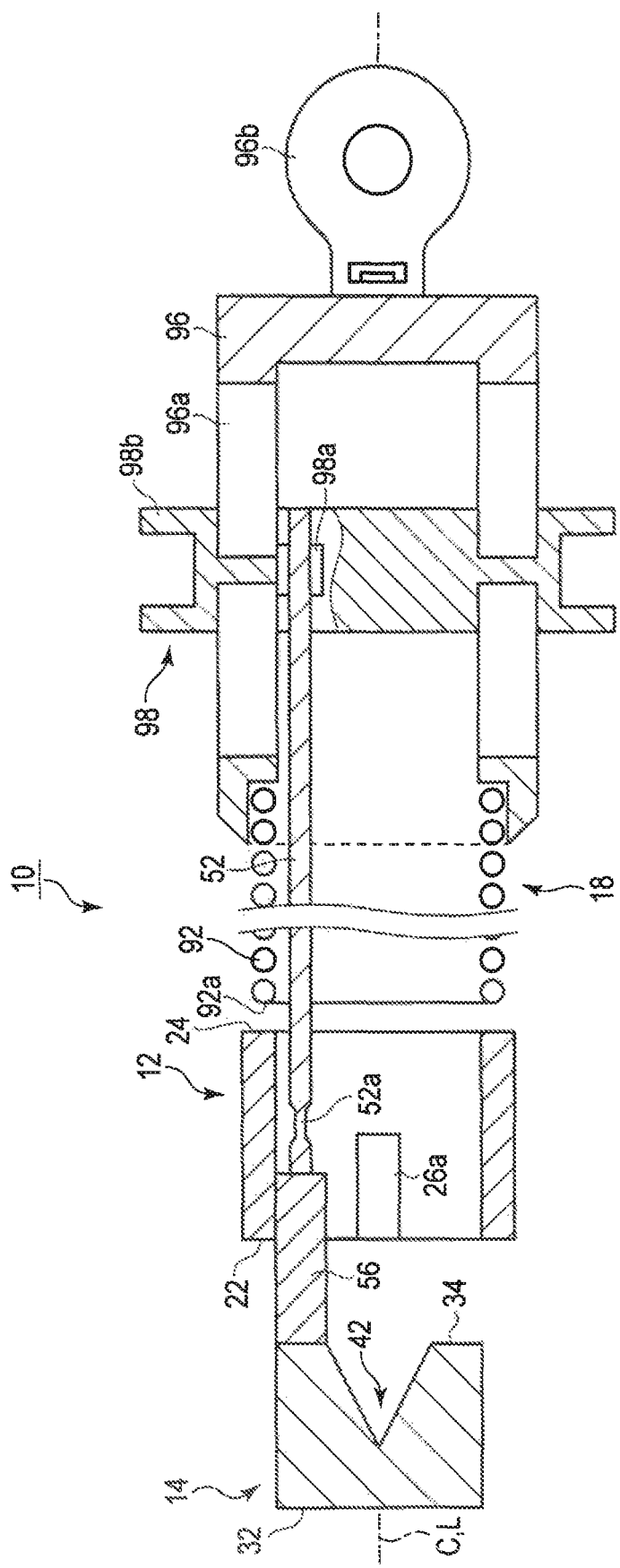
FIG. 9B is a schematic view showing a securing portion having a protrusion to be engaged with the cylindrical body of the suture securing instrument, and the wire connected to the protrusion.

When moving the securing portion 14 relative to the cylindrical body 12 of the suture securing instrument 10, it is preferable that the suture securing instrument 10 includes an applicator 18 shown in FIG. 9A.

The applicator 18 includes a sheath (insertion portion) 92 through which the wire 52 is inserted, and an operation portion 94 disposed on the proximal end side of the sheath 92 and configured to move the wire 52 relative to the sheath 92 in an axial direction of the sheath 92. The sheath 92 is preferably a coil sheath formed in a coil shape. The coil sheath 92 exhibits appropriate flexibility against an external force from the direction deviated from the axial direction, and exerts an axial force in the axial direction. The operation portion 94 includes a base 96 having a slit 96a and a movable portion 98 movable in the axial direction (to a distal end side and to a proximal end side) of the slit 96a of the base 96. The proximal end of the wire 52 is fixed to the movable portion 98 by a securing portion 98a such as swaging. The base 96 has at its proximal end, for example, a ring-shaped finger rest 96b on which a thumb or the like of the user is placed. The movable portion 98 includes a finger rest 99b on which an index finger and/or a middle finger are placed.

The movable portion 98 is movable relative to the base 96 in the direction along the central axis C. Therefore, when the movable portion 98 is moved relative to the base 96 along the central axis C, the wire 52 and the securing portion 14 move relative to the base 96, the sheath 92, and the cylindrical body 12.

When the movable portion 98 is moved toward the proximal end of the base 96 to pull the wire 52, the securing portion 14 moves relative to the cylindrical body 12, and the securing portion 14 fits in the cylindrical body 12. When the movable portion 98 is further moved to the proximal end side to pull the wire 52, the other end 24 of the cylindrical body 12 is brought into contact with the distal end 92a of the sheath 92.

When the suture securing instrument 10 is introduced into a body cavity using the endoscope 102, the suture securing instrument 10 having the applicator 18 is preferably inserted into the treatment instrument insertion channel 114, while the other end 24 of the cylindrical body 12 is being in contact with the distal end 92a of the sheath 92. At this time, the cylindrical body 12 and the securing portion 14 are prevented from being unstable with respect to the distal end 92a of the sheath 92.

When the movable portion 98 is moved to the distal end side of the slit 96a of the base 96, the pulling of the wire 52 is temporarily released. For this reason, the securing portion 14 separated from the cylindrical body 12, and the suture 16 can be disposed in the holding portion 42 of the securing portion 14. At this time, the proximal end 24a of the cylindrical body 12 is released from the distal end 92a of the sheath 92.

When the movable portion 98 is moved to the proximal end side of the base 96 again and the wire 52 is pulled, the securing portion 14 is moved relative to the cylindrical body 12 and fitted in the cylindrical body 12. Thus, the suture securing instrument 10 can appropriately secure the suture 16 to the securing portion 14. In this state, when the movable portion 98 is moved to further pull the wire 52, the other end 24 of the cylindrical body 12 is brought into contact with the distal end 92a of the sheath 92. When the movable portion 98 is moved in this state to further pull the wire 52, the small diameter portion 52a of the wire 52 is broken. With the breakage of the wire 52, the cylindrical body 12 and the securing portion 14 to which the suture 16 is fixed are detached from the distal end 92a of the sheath 92.

When the suture securing instrument 10 is inserted into the treatment instrument insertion channel 114 of the endoscope 102, the other end 24 of the cylindrical body 12 and the distal end 92a of the sheath 92 are preferably in secure contact with each other. For this reason, it is also preferable that the other end 24 of the cylindrical body 12 and the distal end 92a of the sheath 92 be connected by easily removable adhesion. In this case, for example, when an external force is applied to the distal end 92a of the sheath 92 and/or the cylindrical body 12 in a direction deviated from the central axis C, the connection is released.

As shown in FIG. 9E, it is also preferable that a protrusion 56 be formed at the second end 34 of the securing portion 14. The protrusion 56 is fitted in the cylindrical body 12 when the securing portion 14 is to be fitted to the cylindrical body 12. The distal end of the wire 52 is preferably secured to the protrusion 56. Thus, when fitting the securing portion 14 in the cylindrical body 12, the securing portion 14 can be reliably pulled into the cylindrical body 12 of the suture securing instrument 10 without considering the directions of the cylindrical body 12 and the securing portion 14.

As described above, according to the suture securing instrument 10 of this embodiment, the following advantages can be obtained.

As shown in FIGS. 6A and 6E, the suture 16 is supported in a state of being locked and/or held on the suture securing instrument 10. At this time, the suture 16 is maintained in a supported state by holding (securing) by the holding portion 42 and locking between the cuter circumferential surface 36 of the securing portion 14 and the inner circumferential surface 26 of the cylindrical body 12. Then, when the securing portion 14 is supported by the cylindrical body 12, the suture 16 is naturally drawn to an appropriate position of the holding portion 42 of the securing portion 14. Therefore, depending on the size of the cylindrical body 12, the size of the securing portion 14, and the size (outside diameter) of the suture 16, the support position of the securing portion 14 with respect to the cylindrical body 12 may vary along the longitudinal axis L (central axis C). Therefore, the suture securing instrument 10 according to the present embodiment can be less affected by the dimensional tolerance of the cylindrical body 12, the securing portion 14, and the suture 16. In addition, by using the suture securing instrument 10 according to the present embodiment, the suture 16 can be secured with a stable securing force.

Furthermore, the inner circumferential surface 26 of the cylindrical body 12 locks the suture 16 together with the outer circumferential surface 36 of the securing portion 14. Therefore, when tension is applied to the suture 16, the suture 16 can be prevented from being slipped from the holding portion 42 and the holding (fixing) can be maintained.

Even when the wire 52 receives a tension such that the small diameter portion (breakable portion) 52a of the wire 52 may be broken, the suture 16 and the suture securing instrument 10 can maintain the state shown in FIGS. 5A and 5B.

In the example of the present embodiment described above, the securing portion 14 is supported on the cylindrical body 12 by pulling the wire 52 with the forceps 104. Of course, the securing portion 14 may be supported on the cylindrical body 12 by pushing the securing portion 14 into the cylindrical body 12 using the forceps 104 and 106. In this case, the wire 52 may be unnecessary. The direction in which the suture 16 is secured changes depending on the treatment. For this reason, it is preferable that the wire 52 be connected to the securing portion 14.

Next, described below is a mechanism for cutting the wire 52 secured to the securing portion 14 of the suture securing instrument 10 using the cutting mechanism 210 disposed on the inner circumferential surface 26 of the cylindrical body 12. Here, an example in which the cutting mechanism 210 is provided on the inner circumferential surface 26 of the cylindrical body 12 will be described. However, it is also preferred that a similar mechanism be provided in the vicinity of the distal end of the inner circumferential surface of the sheath 92 of the applicator 18 described above (see FIG. 9A). The cutting mechanism 21 described below is provided on the cylindrical body 12 and/or the applicator 18. That is, the cutting mechanism 210 is provided on at least one of the cylindrical body 12 and the applicator 18.

A first mechanism of the cutting mechanism 210 will be described with reference to FIG. 10.

Figure 10:
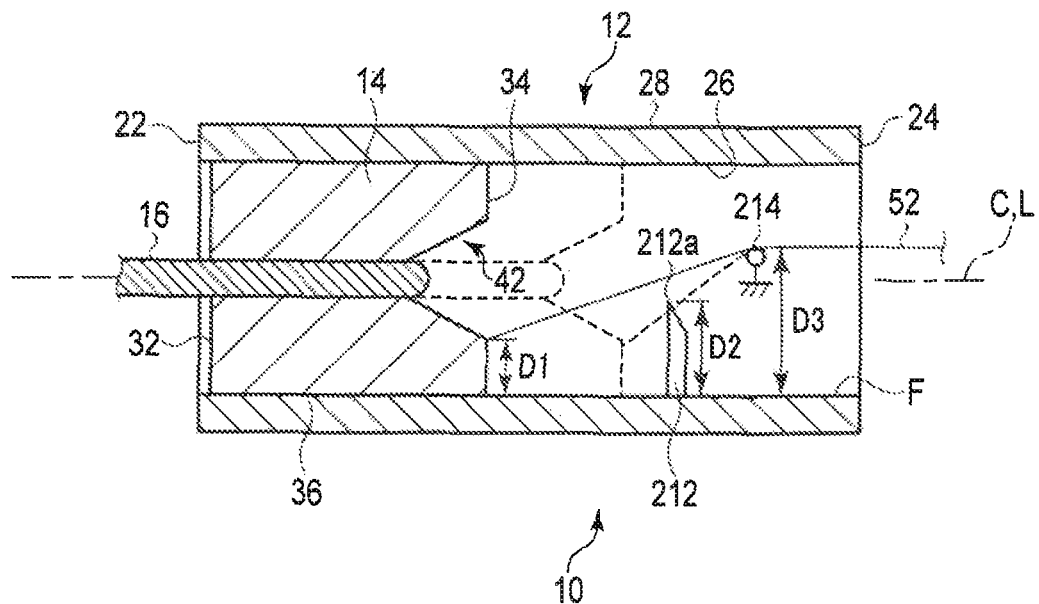
FIG. 10 is a schematic view showing an exemplary mechanism of a cutting mechanism for cutting a wire of the suture securing instrument.

As shown in FIG. 10, the cutting mechanism 210 includes a cutter 212 and a wire support 214. The wire support 214 is disposed at a position close to the other end (proximal end) 24 of the cylindrical body 12. The cutter 212 is located closer to the one end (distal end) 22 of the cylindrical body 12 than the wire support 214.

The fixed position of the wire 52 with respect to the securing portion 14 is a position at the distance D1 from a position (reference position, indicated by the symbol F in FIG. 10) parallel to the central axis C. The reference position F is a position where the fixing position of the wire 52 with respect to the securing portion 14 is closest to the inner circumferential surface 26 of the cylindrical body 12. A blade 212a of the cutter 212 is located at a distance D2 from the reference position F. The wire support 214 is located at a distance D3 from the reference position F. The distance D2 is larger than the distance D1. The distance D3 is larger than the distance D2.

As shown by a solid line in FIG. 10, when the position of the second end (proximal end) 34 of the securing portion 14 is far from the other end 24 of the cylindrical body 12, the wire 52 and the blade 212a of the cutter 212 are spaced apart. When the second end 34 of the securing portion 14 is brought close to the other end 24 of the cylindrical body 12 by pulling the wire 52 as shown by a broken line in FIG. 10, the wire 52 is brought into contact with the blade 212a of the cutter 212. When the second end 34 of the securing portion 14 is brought closer to the other end 24 of the cylindrical body 12, the wire 52 is pressed against the blade 212a of the cutter 212. Thus, the wire 52 is cut by the blade 212a of the cutter 212.

It is also preferable that both the cutter 212 and the wire support 214 be provided on the inner circumferential surface of the sheath 92 of the applicator 18 instead of the inner circumferential surface 26 of the cylindrical body 12. It is also preferable that the cutter 212 be provided on the inner circumferential surface 26 of the cylindrical body 12, while the wire support 214 be provided on the inner circumferential surface of the sheath 92 of the applicator 18.

A second mechanism of the cutting mechanism 210 will be described with reference to FIG. 11.

Figure 11:
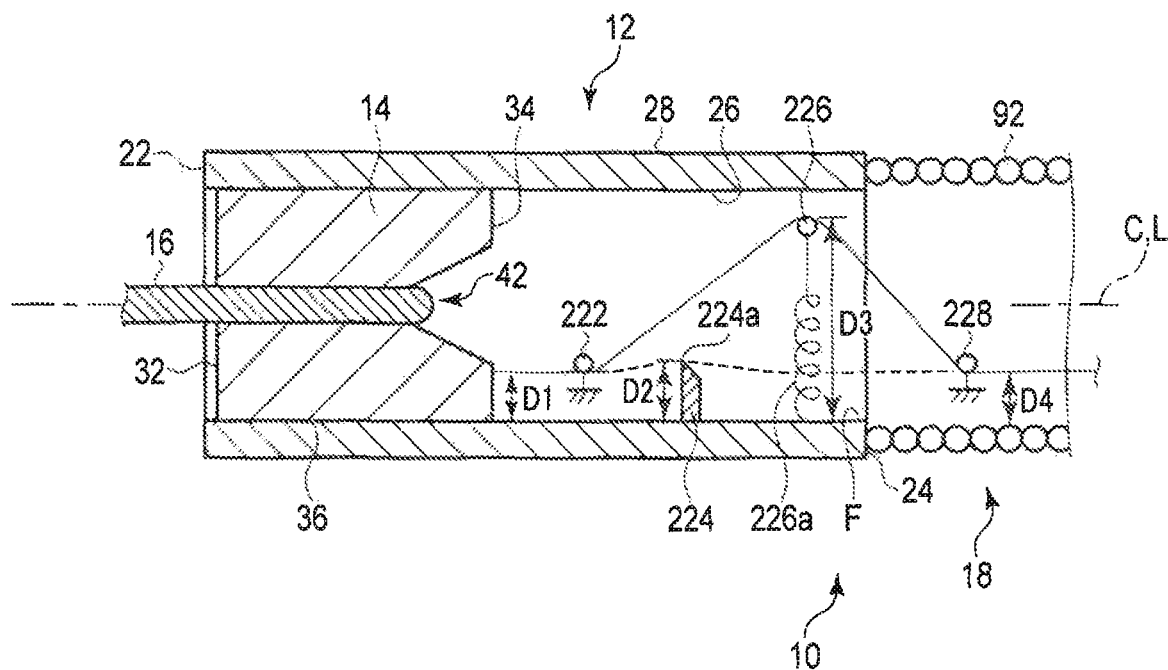
FIG. 11 is a schematic view showing an exemplary mechanism of a cutting mechanism for cutting a wire of the suture securing instrument.

As shown in FIG. 11, the cutting mechanism 210 includes a first wire support 222, a cutter 224, a second wire support 226, and a third wire support 228. The second wire support 226 is urged toward a position opposite to the reference position F or in the vicinity thereof by an urging member (elastic member) 226a, such as a spring. In this embodiment, the third wire support 228 is disposed on the inner circumferential surface of the sheath 92 of the applicator 18 (see FIG. 9A), but may be disposed on the inner circumferential surface 26 of the cylindrical body 12.

The fixed position of the wire 52 with respect to the securing portion 14 and the position of the first wire support 222 are at the distance D1 from the reference position. F in FIG. 11. A blade 224a of the cutter 224 is located at a distance D2 from the reference position F. The second wire support 226 is located at a distance D3 from the reference position F. The third wire support 228 is located at a distance D4 from the reference position F. The distance D2 is larger than the distance D1. The distance D3 is larger than the distance D2. The distance D4 is smaller than the distance D3. The distance D3 can be varied by the urging member 226a.

As shown in FIG. 11, when the wire 52 is further pulled in a state in which the position of the securing portion 14 is fixed with respect to the cylindrical body 12, the tension of the wire 52 is increased. Therefore, the wire 52 approaches the reference position F against the urging force of the urging member 226a of the second wire support 226, and the wire 52 is brought into contact with the blade 224a of the cutter 224. As the wire 52 is further pulled and tension increases, the wire 52 is pressed against the blade 224a of the cutter 224. Thus, the wire 52 is cut by the blade 224a of the cutter 224.

A third mechanism of the cutting mechanism 210 will be described with reference to FIG. 12A and FIG. 12B.

Figure 12A:
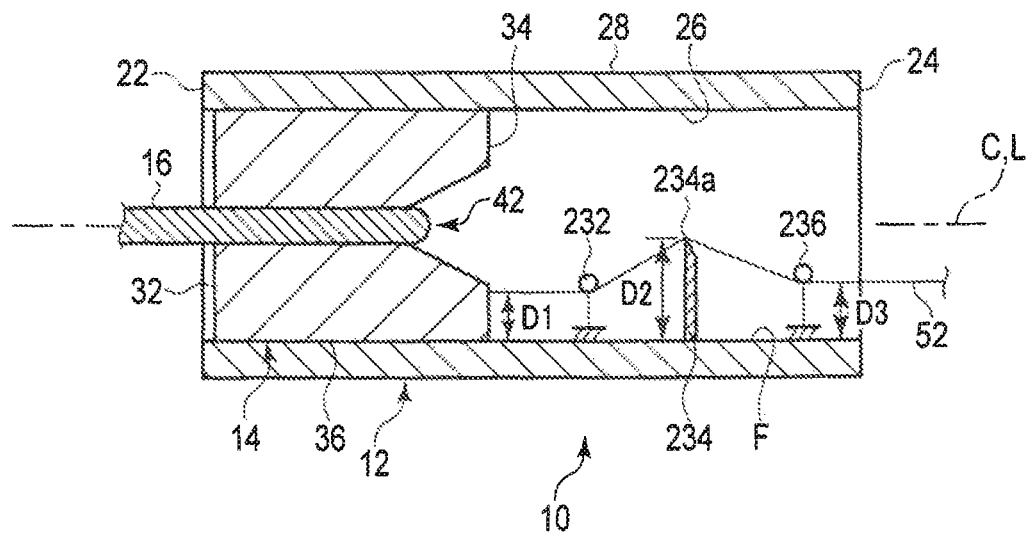
FIG. 12A is a schematic view showing an exemplary mechanism of a cutting mechanism for cutting a wire of the suture securing instrument.
Figure 12B:
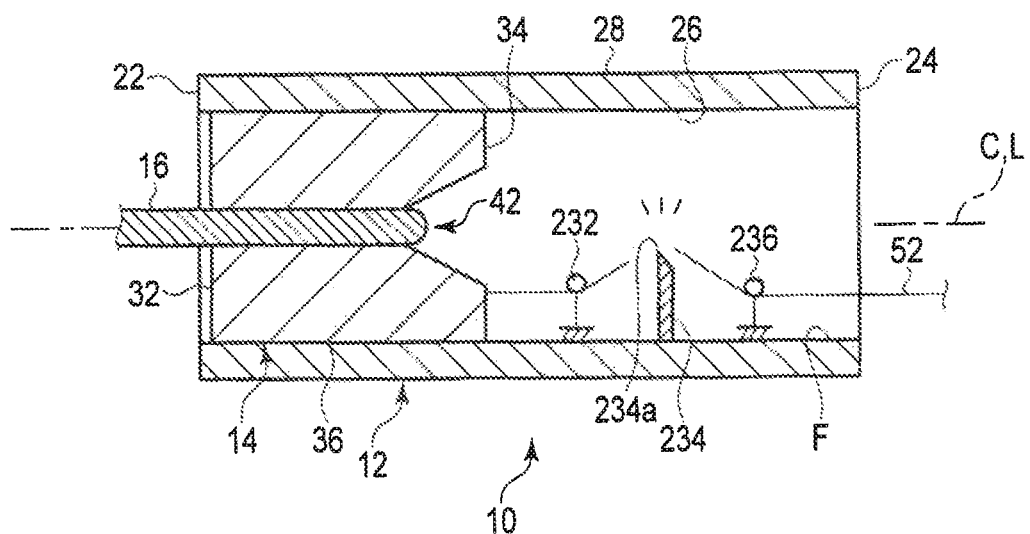
FIG. 12B is a schematic view showing a state in which the wire of the suture securing instrument is cut using the exemplary mechanism of the cutting mechanism shown in FIG. 12A.

As shown in FIGS. 12A and 12B, the cutting mechanism 210 includes a first wire support 232, a cutter 234, and a second wire support 236.

The fixed position of the wire 52 with respect to the securing portion 14 and the position of the first wire support 232 are at the distance D1 from the reference position F in FIG. 12A. A blade 234a of the cutter 234 is located at a distance D2 from the reference position F. The second wire support 236 is located at a distance D3 from the reference position F. The distance D2 is larger than the distance D1. The distance D3 is smaller than the distance D2.

As shown in FIG. 12A, the wire 52 is always in contact with the blade 234a of the cutter 234. When the wire 52 is further pulled in a state in which the position of the securing portion 14 is fixed with respect to the cylindrical body 12, the tension of the wire 52 is increased. Therefore, the wire 52 pressed against the blade 234a of the cutter 234. Thus, as shown in FIG. 13, the wire 52 is cut by the blade 2:34a of the cutter 234.

A fourth mechanism of the cutting mechanism 210 will be described with reference to FIG. 13.

Figure 13:
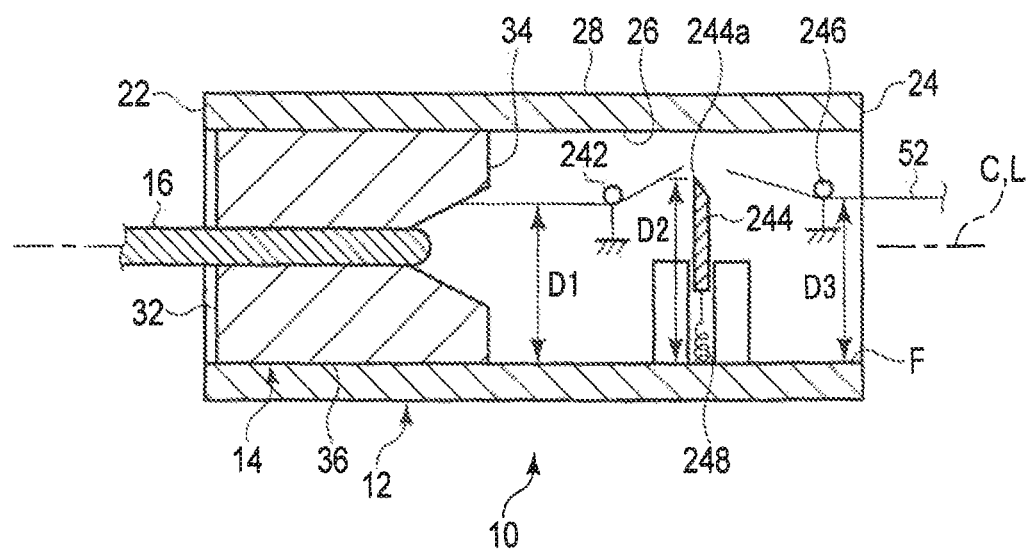
FIG. 13 is a schematic view showing a state in which the wire of the suture securing instrument is cut using an exemplary mechanism of the cutting mechanism for cutting the wire of the suture securing instrument.

As shown in FIG. 13, the cutting mechanism 210 includes a first wire support 242, a cutter 244, and a second wire support 246. A blade 244a of the cutter 244 is urged toward the position opposite to the reference position F or in the vicinity thereof by an urging member 248, such as a spring.

The fixed position of the wire 52 with respect to the securing portion 14 and the position of the first wire support 242 are at the distance D1 from the reference position F in FIG. 13. The blade 244a of the cutter 244 is located at a distance D2 from the reference position F. The second wire support 246 is located at a distance D3 from the reference position F. The distance D2 is larger than the distance D1. The distance D3 is smaller than the distance D2. The distance D2 is variable.

The wire 52 is always in contact with the blade 244a of the cutter 244. When the wire 52 is further pulled in a state in which the position of the securing portion 14 is fixed with respect to the cylindrical body 12, the tension of the wire 52 is increased. Therefore, the wire 52 is pressed against the blade 244*a* of the cutter 244. Therefore, as shown in FIG. 13, the wire 52 is cut by the blade 244*a* of the cutter 244 due to the urging force of the urging member 248.

A fifth mechanism of the cutting mechanism 210 will be described with reference to FIG. 14A and FIG. 14B.

Figure 14A:
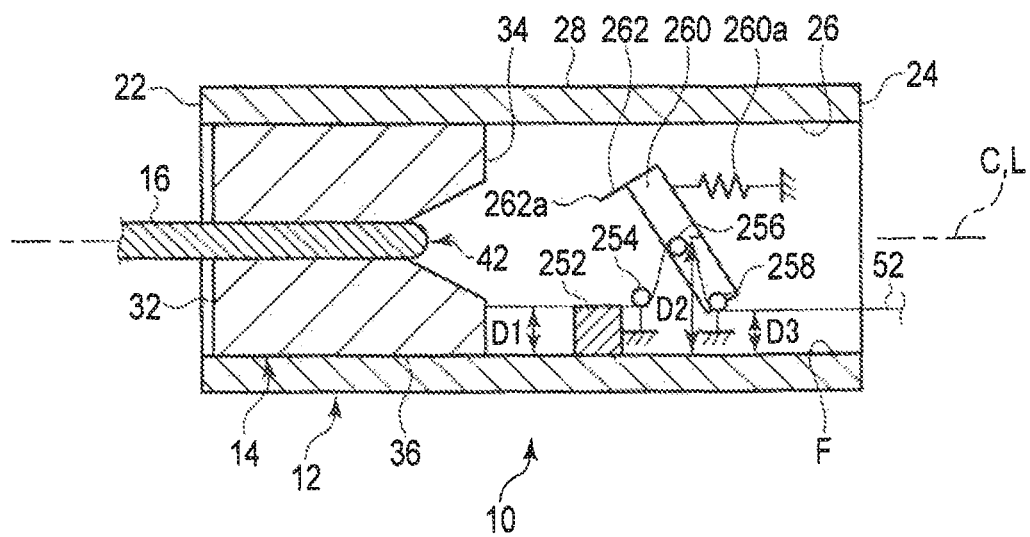
FIG. 14A is a schematic view showing an exemplary mechanism of a cutting mechanism for cutting a wire of the suture securing instrument.
Figure 14B:
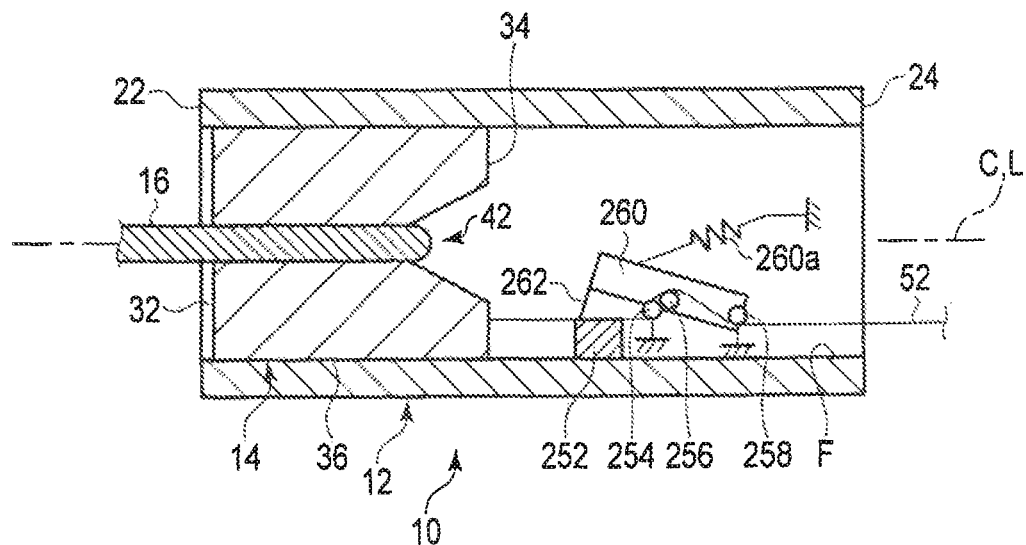
FIG. 14B is a schematic view showing a state in which the wire of the suture securing instrument is cut using the fifth mechanism of the cutting mechanism shown in FIG. 14A.

As shown in FIG. 14A, the cutting mechanism 210 includes a blade rest 252, a first wire support 254, a second wire support 256, a third wire support 258, and a pivoting member 260, and a cutter 262.

The second wire support 256 is provided on the pivoting member 260. The pivoting member s pivotally supported by the third wire support 258. The pivoting member 260 is urged by an urging member 260*a*, such as a spring, so that the blade 262*a* of the cutter 262 is separated from the blade rest 252.

The fixed position of the wire 52 with respect to the securing portion 14 and the position of the first wire support 254 are at the distance D1 from the reference position F in FIG. 14A. The second wire support 256 is located at a distance D2 from the reference position F. The third wire support 258 is located at a distance D3 from the reference position F. The distance D2 is larger than the distance D1. The distance D3 is smaller than the distance D2. The blade holder 252 is preferably located at a distance equal to or smaller than the distance D1 from the reference position F. The wire 52 is placed on the blade rest 252.

When the wire 52 is further pulled in a state in which the position of the securing portion 14 is fixed with respect to the cylindrical body 12, the tension of the wire 52 is increased. The wire 52 brings the second wire support 256 close to the reference position F against the urging force of the urging member 260*a*. At this time, the blade 262*a* of the cutter 262 approaches the blade rest 252. As the wire 52 is pulled further, the tension of the wire 52 increases. Thus, the wire 52 placed on the blade rest 252 is caught and cut by the blade 262*a* of the cutter 262.

A sixth mechanism of the cutting mechanism 210 will be described with reference to FIG. 15A and FIG. 153.

Figure 15A:
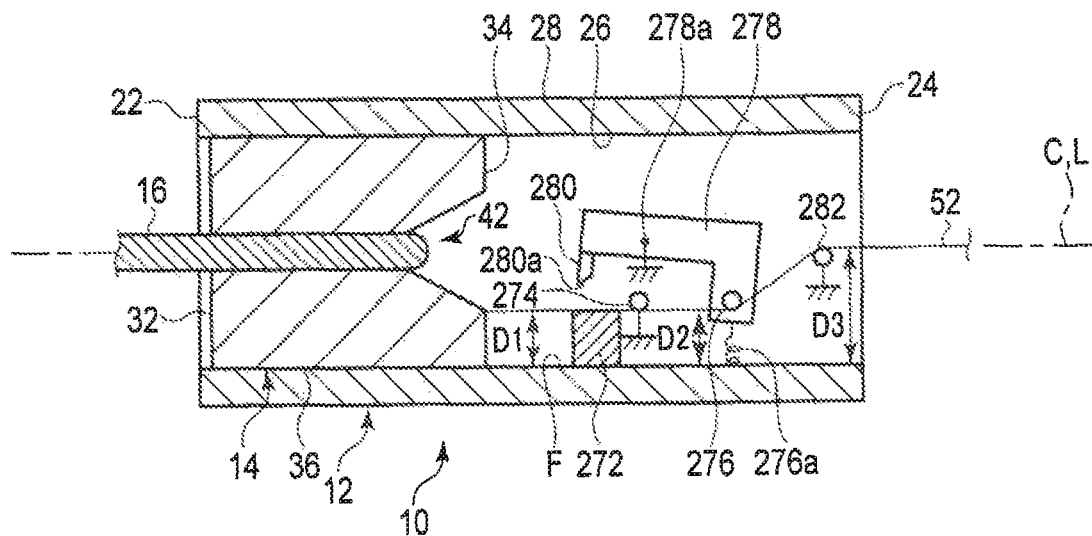
FIG. 15A is a schematic view showing a sixth mechanism of a cutting mechanism for cutting a wire of the suture securing instrument.

As shown in FIG. 15A, the cutting mechanism 210 includes a blade rest 272, a first wire support 274, a second wire support 276, a pivoting member 278, a cutter 280, and a third wire support 282.

The pivoting member 278 is pivotally supported to the cylindrical body 12 by a support shaft 278*a*. The second wire support 276 is supported by an urging member 276*a*, such as a spring. The second wire support 276 is provided on the pivoting member 278. Therefore, the pivoting member 278 is urged by the urging member 276*a* such that the blade 280*a* of the cutter 280 is separated from the blade rest 272.

The fixed position of the wire 52 with respect to the securing portion 14 and the position of the first wire support 274 are at the distance D1 from the reference position F in FIG. 15A. The second wire support 276 is located at a distance D2 from the reference position F. The third wire support 282 is located at a distance D3 from the reference position F. The distance D2 is equal to or smaller than the distance D1. The distance D3 is larger than the distance D2. The blade rest 272 is preferably located at a distance equal to or smaller than the distance D1 from the reference position F. The wire 52 is placed on the blade holder 272.

When the wire 52 is further pulled in a state in which the position of the securing portion 14 is fixed with respect to the cylindrical body 12, the tension of the wire 52 is increased. The wire 52 moves the second wire support 276 away from the reference position F against the urging force of the urging member 276*a*. At this time, the pivoting member 278 pivots around the axis of the support shaft 278*a*, and the blade 280*a* of the cutter 280 approaches the blade rest 272. As the wire 52 is pulled further, the tension of the wire 52 increases. Thus, the wire 52 placed on the blade rest 272 is caught and cut by the blade 280*a* of the cutter 280.

A modification of the shapes of the cylindrical body 12 and the securing portion 14 will be explained. In the examples shown in FIGS. 16A to 160, the suture 16 is omitted.

In the example shown in FIG. 1A to FIG. 6B, the inner circumferential surface 26 in the cross section orthogonal to the central axis C of the cylindrical body 12 is substantially rectangular. In the example shown in FIG. 16A, the inner circumferential surface 26 in the cross section orthogonal to the central axis C of the cylindrical body 12 is substantially annular.

In the example shown in FIGS. 1A to 6B, the outer circumferential surface 36 in the cross section orthogonal to the longitudinal axis L of the securing portion 14 is substantially rectangular. In the example shown in FIG. 16A, the outer circumferential surface 36 in the cross section orthogonal to the longitudinal axis L of the securing portion 14 is substantially circular.

In the example shown in FIG. 1A to FIG. 6B, the outer circumferential surface 28 in the cross section orthogonal to the central axis C of the cylindrical body 12 substantially rectangular. In the example shown in FIG. 16A, the outer circumferential surface 28 in the cross section orthogonal to the central axis C of the cylindrical body 12 is substantially elliptical.

Figure 16B:
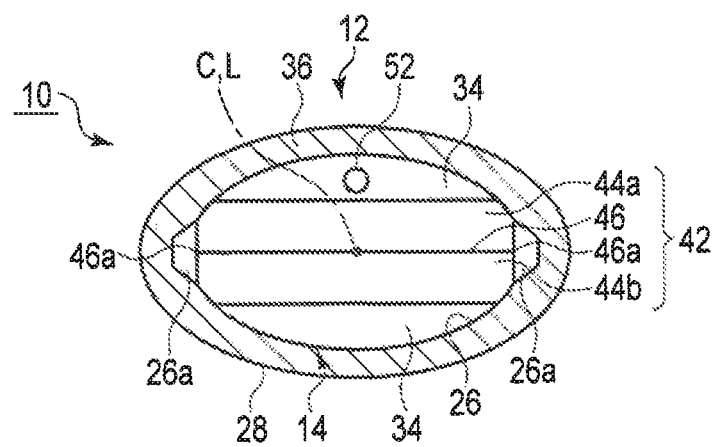
FIG. 16B is a schematic view of a suture securing instrument having an external shape different from that shown in FIG. 1D and FIG. 16A, showing a cross section of a cylindrical body having an elliptical inner wall and an elliptical columnar securing portion.

The inner circumferential surface 26 in the cross section orthogonal to the central axis C of the cylindrical body 12 of the example shown in FIG. 16B is substantially elliptical. The outer circumferential surface 36 in the cross section orthogonal to the longitudinal axis L of the securing portion 14 is substantially elliptical.

Figure 16C:
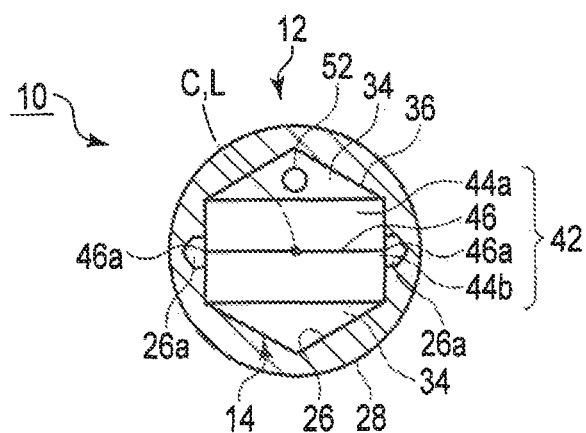
FIG. 16C is a schematic view of a suture securing instrument having an external shape different from that shown in FIG. 1D, FIG. 16A and FIG. 163, showing a cross section of a cylindrical body having a hexagonal inner wall and a hexagonal columnar securing portion.

The inner circumferential surface 26 in the cross section orthogonal to the central axis C of the cylindrical body 12 of the example shown in FIG. 16C is substantially hexagonal. The outer circumferential surface 36 in the cross section orthogonal to the longitudinal axis L of the securing portion 14 is substantially hexagonal.

In addition, the outer circumferential surface 28 in the cross section orthogonal to the central axis C of the cylindrical body 12 of the example shown in FIG. 16C does not need to be substantially hexagonal, and is circular.

Thus, the cross section orthogonal 4*o* the central axis C of the inner circumferential surface 26 of the cylindrical body 12 is not limited to the substantially rectangular shape shown in FIGS. 1A to 6B, but may be any appropriate shape, for example, a circular shape, (see FIG. 16A), an elliptical shape (see FIG. 16B), or an appropriate polygonal shape (see FIG. 16C). Further, the cross section orthogonal to the central axis C of the outer circumferential surface 28 of the cylindrical body 12 is not limited to the same shape as that of the inner circumferential surface 26, and any appropriate shape may be adopted. Furthermore, the cross section orthogonal to the longitudinal axis L of the securing portion 14 is not limited to a substantially rectangular shape, but may be any appropriate polygon, ellipse, circle, etc. according to the shape of the inner circumferential surface 26 of the cylindrical body 12. In addition, although not shown, for example, if the securing portion 14 is a pentagonal prism, it is also preferable that the holding portion 42 be formed between an apex and a side facing each other about the longitudinal axis L at the second end 34.

In the following, a modification of the structure for supporting the securing portion 14 to the cylindrical body 12 will be explained.

Figure 17A:
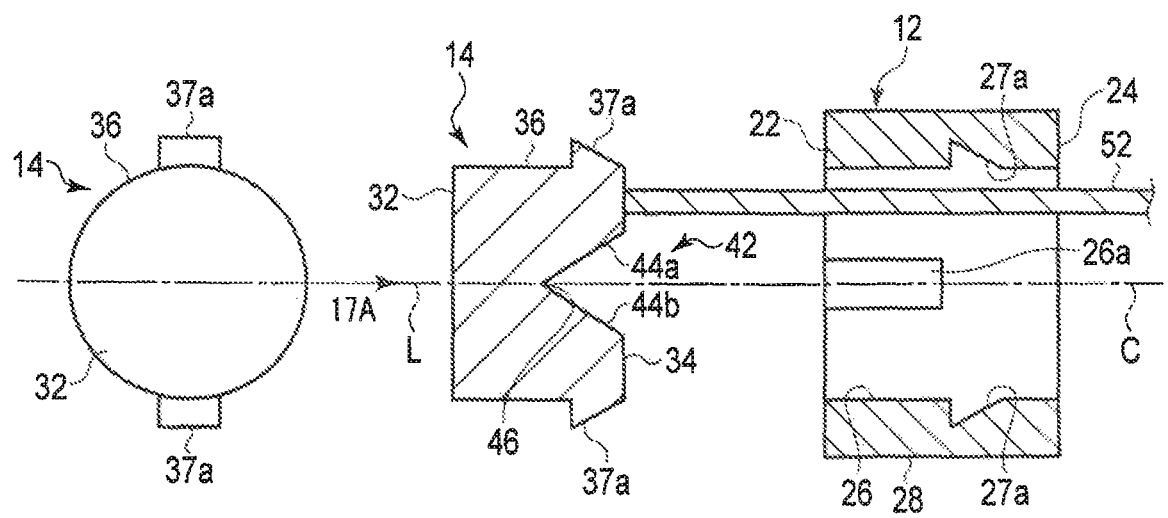
FIG. 17A is a schematic view showing a cross section of a suture securing instrument in which a cylindrical body having an engaging portion and a securing portion having an engaging portion are separated, which are different from the cylindrical body and the stationary portion of the suture securing instrument shown in FIG. 1A, and also showing the securing portion viewed from the direction indicated by an arrow 17A.
Figure 17B:
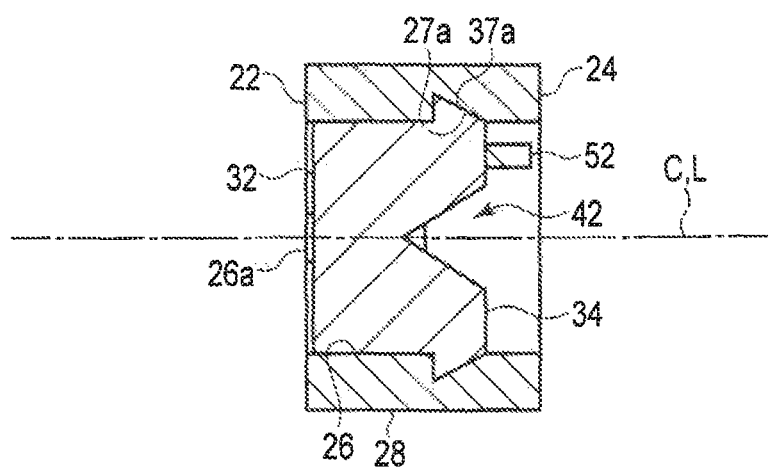
FIG. 17B is a schematic view showing a cross section of the suture securing instrument shown in FIG. 17A in which the engagement portions of the cylindrical body and the securing portion are engaged.

As shown in FIGS. 17A and 17B, for example, in the vicinity of the other end 24 of the cylindrical body 12, an engagement concave portion (engagement portion) 27a that suppresses movement of the securing portion 14 through the other end 24 of the cylindrical body 12 is formed. In the vicinity of the second end (end face) 34 of the securing portion 14, an engagement convex portion (engagement portion) 37a that engages with the engagement concave portion 27a is formed. In this example, a pair of engagement concave portions 27a and a pair of engagement convex portions 37a are provided. In this case, the securing portion 14 is engaged with the cylindrical body 12 at a predetermined position in the direction around the longitudinal axis L of the securing portion 14 with respect to the cylindrical body 12. For this reason, the state where the securing portion 14 is engaged and supported with respect to the cylindrical body 12 is stably maintained.

In addition, the materials of the cylindrical body 12 and the securing portion 14 are suitably selected so that the securing portion 14 can be supported with respect to the cylindrical body 12. In the case where the cylindrical body 12 is a metal material, it is preferable that in particular, the engaging convex portion 37a of the securing portion 14 be formed of a resin material or a rubber material that can be elastically deformed larger than the metal material used for the cylindrical body 12. In the case where the engagement convex portion 37a of the securing portion 14 is a metal material, it is preferable that the cylindrical body 12 be formed of a resin or rubber material that can be elastically deformed larger than the metal material of the engagement convex portion 37a of the securing portion 14.

As shown in FIGS. 18A and 18B, the engagement convex portion (engagement portion) 37a of the securing portion 14 is formed over the entire circumference of the edge portion of the second end (end surface) 34. The inner circumferential surface 26 of the cylindrical body 12 is formed to have the same cross-sectional shape from the one end 22 to the other end 24 of the cylindrical body 12. Therefore, unlike the example shown in FIG. 17A and FIG. 17B, the engagement convex portion 37a of the securing portion 14 may be formed over the entire circumference of the edge of the second end 34 of the securing portion 14. In this case, the engagement convex portion 37a of the securing portion 14 is press-fitted from the one end 22 of the cylindrical body 12 toward the other end 24. The inner circumferential surface 26 of the cylindrical body 12 and the outer circumferential surface 36 of the securing portion 14 are suppressed from moving along the longitudinal axis L and the central axis C by friction, or rotating around the longitudinal axis L and the central axis C.

In the case where the cylindrical body 12 is a metal material, it is preferable that in particular, the engaging convex portion 37a of the securing portion 14 be formed of a resin material or a rubber material that can be elastically deformed larger than the metal material used for the cylindrical body 12. In the case where the engagement convex portion 37a of the securing portion 14 is a metal material, it is preferable that the cylindrical body 12 be formed of a resin or rubber material that can be elastically deformed larger than the metal material of the engagement convex portion 37a of the securing portion 14.

In the example shown in FIGS. 18A and 18B, as in the example shown in FIGS. 17A and 17B, the materials of the cylindrical body 12 and the securing portion 14 can be appropriately selected to allow the securing portion 14 to be supported to the cylindrical body 12.

Figure 19A:
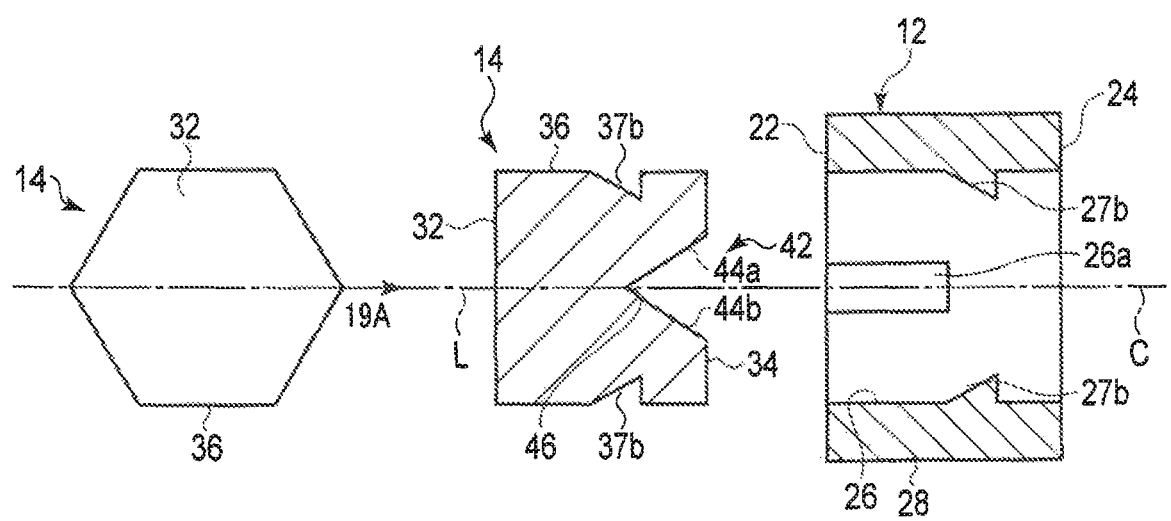
FIG. 19A is a schematic view showing a cross section of a suture securing instrument in which a cylindrical body having an engaging portion and a securing portion having an engaging portion are separated, which are different from the cylindrical body and the stationary portion of the suture securing instrument shown in FIG. 1A, FIG. 17A and FIG. 18A, and also showing the securing portion viewed from the direction indicated by an arrow ISA.
Figure 19B:
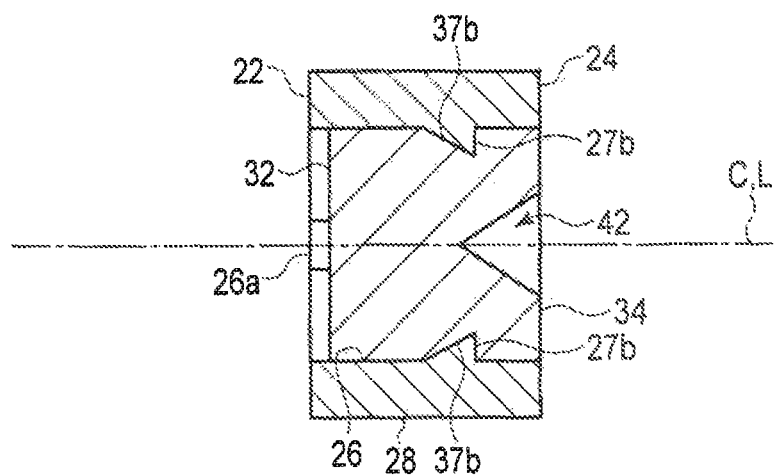
FIG. 19B is a schematic view showing a cross section of the suture securing instrument shown in FIG. 19A in which the engagement portions of the cylindrical body and the securing portion are engaged.

As shown in FIGS. 19A and 19B, on the inner circumferential surface 26 of the cylindrical body 12, an engagement convex portion (engagement portion) 27b is formed. An engagement concave portion (engagement portion) 37b is formed on the outer circumferential surface 36 of the securing portion 14. The engagement convex portion 27b of the inner circumferential surface 26 of the cylindrical body 12 is engaged with the engagement concave portion 37b of the outer circumferential surface 36 of the securing portion 14. Thus, the state in which the securing portion 14 is engaged and supported with respect to the cylindrical body 12 is stably maintained.

In the example shown in FIGS. 19A and 19B, the materials of the cylindrical body 12 and the securing portion e appropriately selected so that the securing portion 14 can be supported to the cylindrical body 12 as in the example shown in FIGS. 17A and 17B and the example shown in FIGS. 18A and 18B.

Also in the example of the suture securing instrument 10 shown in FIGS. 16A to 19B, the support position of the securing portion 14 with respect to the cylindrical body 12 may vary along the longitudinal axis L (central axis depending on the size of the cylindrical body 12, the size of the securing portion 14, and the size (outside diameter) of the suture 16. Therefore, the suture securing instrument 10 shown in FIG. 16A to FIG. 19B can be less affected by the dimensional tolerance of the cylindrical body 12, the securing portion 14, and the suture 16. Further, by using the suture securing instrument 10 shown in FIG. 16A to FIG. 19B, the suture securing instrument 10 can secure the suture 16 with a stable securing force.

Referring to FIG. 20 to FIG. 23C, the securing portion 14 of the suture securing instrument 10 will be described while appropriately omitting the illustration of the cylindrical body 12 and the suture 16. With respect to the securing portion 14 shown in FIGS. 20 to 23C, the cylindrical body 12 having an appropriate inner circumferential surface 26 can be used in the suture securing instrument 10. In particular, any shape of the inner circumferential surface is applicable as long as a gap slightly smaller than the diameter of the suture 16 is formed between the end 46a of the bottom portion 46 of the holding portion 42 and the inner circumferential surface 26 of the cylindrical body 12, so that the suture 16 can be locked in the gap. Also in the cases of using the securing portions 14 shown in FIGS. 20 to 23C, the support position of the securing portion 14 with respect to the cylindrical body 12 may vary along the longitudinal axis L (central axis C), depending on the size of the cylindrical body 12 the size of the securing portion 14, and the size (outside diameter) of the suture 16. Therefore, by applying an appropriate cylindrical body 12 and the suture 16 to the securing portion 14 shown in FIG. 20 to FIG. 23C, the suture securing instrument can be less affected by the dimensional tolerance of the cylindrical body 12, the securing portion 14, and the suture 16.

A modification of the second end 34 including the holding portion 42 of the securing portion 14 will be described.

Figure 20:
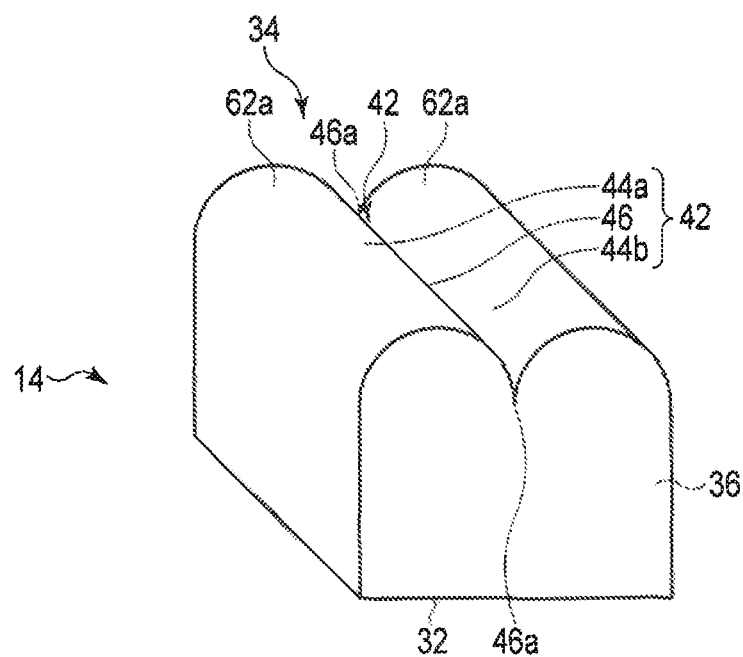
FIG. 20 is a schematic perspective view showing a securing portion of the suture securing instrument, in which the holding portion is formed of a curved surface formed by arranging two semi-cylindrical members at the second end, different from the securing portion shown in FIG. 1A to FIG. 1E.

In the example shown in FIG. 20, the second end (end face) 34 of the securing portion 14 is not flat. Semi-cylindrical members 62a and 62b are arranged at the second end 34 of the securing portion 14 in the direction orthogonal to the longitudinal axis L. The semi-cylindrical members 62a and 62b are preferably the same in shape. In this modification, the holding portion 42 is formed between the semi-cylindrical members 62a and 62b. The guides 44a and 44b of the holding portion 42 are also formed as curved surfaces, not flat surfaces.

The securing portion 14 in this case can also be used in the same manner as the securing portion 14 described in the above-described embodiment.

Figure 21A:
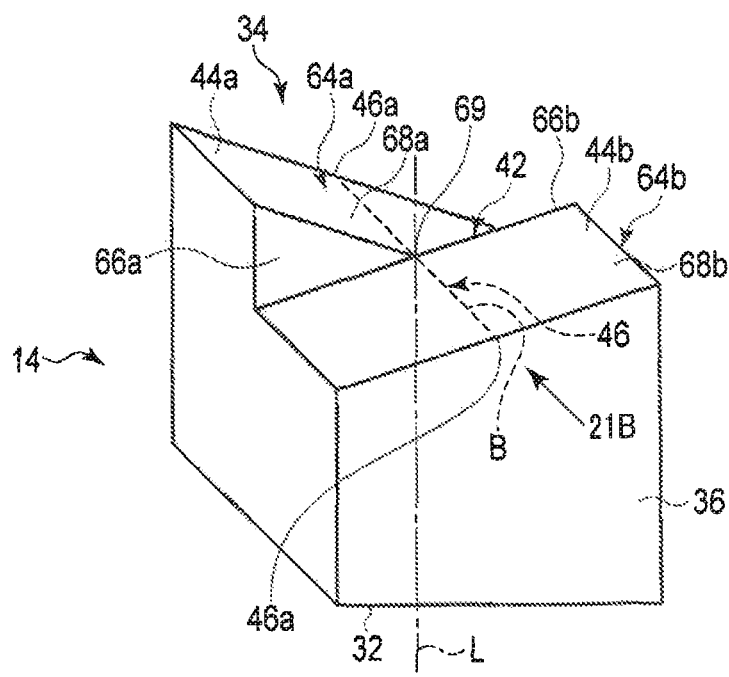
FIG. 21A is a schematic perspective view showing a securing portion of the suture securing instrument, in which the holding portion is formed of two inclined surfaces formed by arranging two triangular prism members at the second end, different from the securing portion shown in FIG. 1A to FIG. 1E.
Figure 21B:
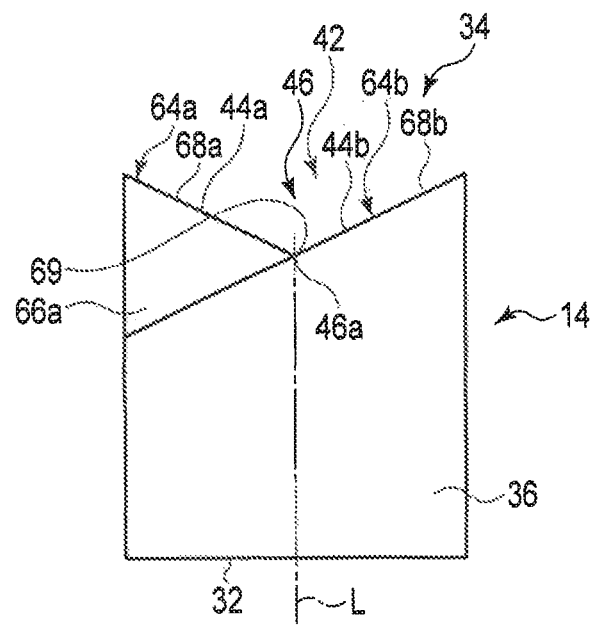
FIG. 21B is a schematic view showing the securing portion of the suture securing instrument shown in FIG. 21A as viewed in a direction indicated by an arrow 21B in FIG. 21A.

In the example shown in FIG. 21A and FIG. 21B, the second end (end face) 34 of the securing portion 14 is not a simple plane, but is uneven. At the second end 34 of the securing portion 14, triangular prism members 64a and 64b are arranged in the direction orthogonal to the longitudinal axis L. The triangular columnar members 64a and 64b include, au the second end 34, two triangular surfaces 66a and 66b parallel to the longitudinal axis L and two rectangular inclined surfaces 68a and 68b intersecting the longitudinal axis L. The two inclined surfaces 68a and 68b form one intersection point 69. The intersection point 69 is defined equally by the two triangular surfaces 66a and 66b and by the two inclined surfaces 68a and 68b. Here, the intersection point 69 is on the longitudinal axis L.

The suture 16 (not shown) is placed at a position passing the intersection point 69 shown by a broken line B in FIG. 21A and orthogonal to the inclination direction of the two inclined surfaces 68a and 68b. At this time, the position indicated by the broken line B is used as the bottom portion 46 of the holding portion 42. Of the inclined surfaces 68a and 68b, portions farther from the position indicated by the broken line B than the first end 32 are used as the guides 44a and 44b of the holding portion 42. In this example, the guides 44a and 44b are in a non-facing position, where they do not face each other.

FIG. 21B shows a view as seen from the direction shown by an arrow 21B in FIG. 21A. The inclined surfaces 68a and 68b are formed in a substantially V shape with the intersection 69 as a bottom portion 46. Thus, the inclined surfaces 68a and 68b define the holding portion 42.

The securing portion 14 in this case can also be used in the same manner as the securing portion 14 described in the above-described embodiment.

Figure 21C:
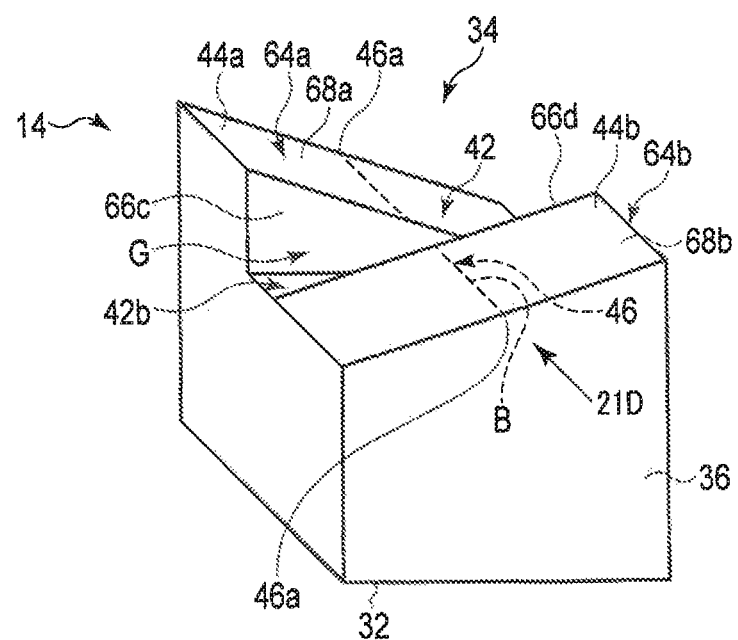
FIG. 21C is a schematic perspective view showing a modification of the securing portion of the suture securing instrument shown in FIG. 21A, in which the holding portion is formed of two inclined surfaces formed by arranging two triangular prism members at the second end.
Figure 21D:
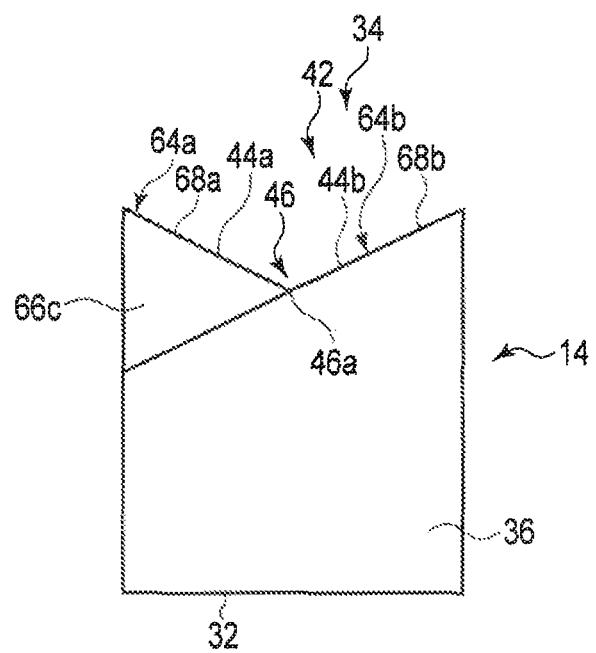
FIG. 21D is a schematic view showing the securing portion of the suture securing instrument show in FIG. 21C as viewed in a direction indicated by an arrow 21D in FIG. 21C.

In the example shown in FIGS. 21C and 21D, the two triangular prism members 64a and 64b are separated. In other words, a gap G (see FIG. 21O) is formed between the two triangular column members 64a and 64b. The triangular columnar members 64a and 64b include, at the second end 34, two rectangular surfaces 66c and 66d formed along the longitudinal axis L and two rectangular inclined surfaces 68a and 68b intersecting the longitudinal axis L.

FIG. 21D shows a view as seen from the direction shown by an arrow 21D in FIG. 21C. The inclined surfaces 68a and 68b are formed in a substantially V-shape. Thus, the inclined surfaces 68a and 68b define the holding portion 42. The inclined surfaces 68a and 68b define the bottom portion 46 of the holding portion 42 when viewed from the direction indicated by the arrow 21D in FIG. 21C. Of the inclined surfaces 68a and 68b, portions farther from the position indicated by the broken line B than the first end 32 are used as the guides 44a and 44b of the holding portion 42.

It is preferable that the gap (distance) G between the two triangular surfaces 66c and 66d narrows toward the first end 32 from the second end 34 of the securing portion 14. The maximum distance between the two triangular faces 66c and 66d is greater than the diameter of the suture 16 used. The distance between the two triangular surfaces 66c and 66d decreases toward the first end 32 from the second end 34 of the securing portion 14, such that it is smaller than the diameter of the suture 16 used. In this case, the spacing between the triangular surfaces 66c and 66d may be used as another holding portion 42b for the suture 16.

The securing portion 14 in this case can also be used in the same manner as the securing portion 14 described in the above-described embodiment.

Figure 22A:
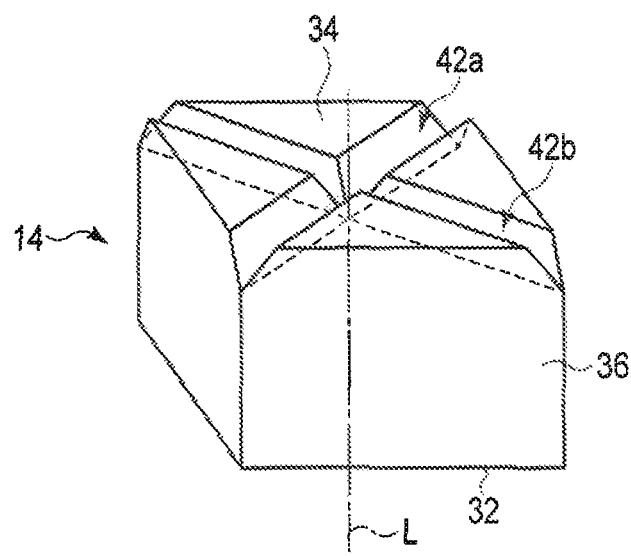
FIG. 22A is a schematic perspective view showing a securing portion of the suture securing instrument, in which two holding portions intersecting each other are formed at the second end of the securing portion to connect apexes of the second end facing each other, different from the securing portion shown in FIG. 1A to FIG. 1E.

In the example shown in FIG. 22A, a plurality of holding portions 42a and 42b are formed at the second end (end face) 34 of the securing portion 14. The holding portions 42a and 42b are formed in the same shape as the holding portion 42 of the securing portion 14 shown in FIGS. 1A to 6B. For this reason, the holding portions 42a and 42b include a plurality of pairs of guides 44a and 44b (see FIG. 5C) for guiding the suture 16 in the direction intersecting the longitudinal axis L. In FIG. 22A, the holding portions 42a and 42b both pass through the longitudinal axis L, but may be offset from the longitudinal axis L.

In the example shown in FIG. 22A, at the second end (end face) 34 of the securing portion 14, the holding portions 42a and 42b are formed between apexes facing each other, centered on the longitudinal axis L.

Figure 22B:
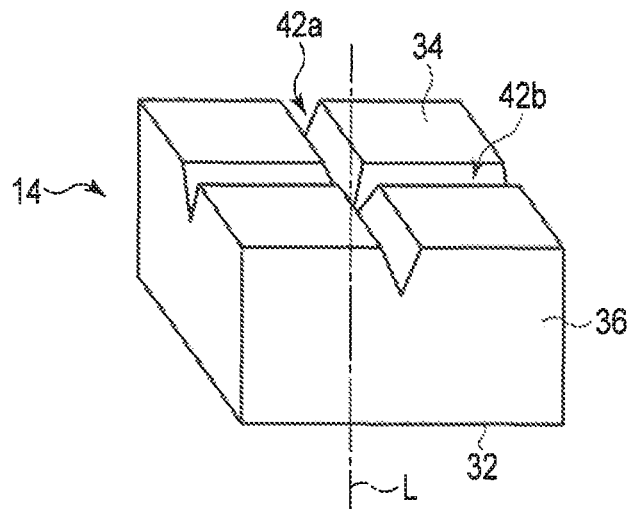
FIG. 22B is a schematic perspective view showing a modification of the securing portion of the suture securing instrument shown in FIG. 22A, in which two holding portions intersecting each other are formed at the second end of the securing portion to connect sides of the second end facing each other.
Figure 22C:
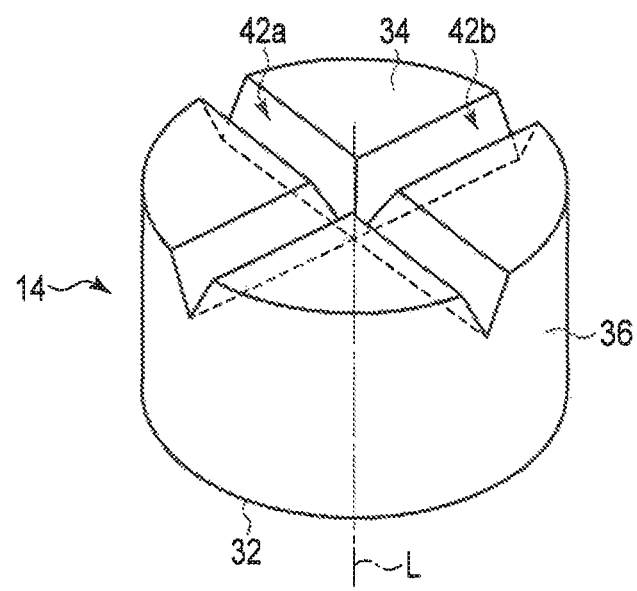
FIG. 22C is a schematic perspective view showing a modification of the securing portion of the suture securing instrument shown in FIG. 22A and FIG. 22B, in which two holding portions intersecting each other are formed at a circular second end at the longitudinal axis of the securing portion.

In the example shown in FIG. 22B, at the second end (end face) 34 of the securing portion 14, the holding portions 42a and 42b are formed between the sides facing each other, centered on the longitudinal axis L. In this case, the holding portions 42a and 42b are preferably orthogonal to each other.

In the example shown in FIG. 22A or 22B, a plurality of (two) holding portions 42a and 42b are formed. In this case, the suture 16 may be guided to any one of the holding portions 42a and 42b. For this reason, in comparison with the examples shown in FIG. 1A to FIG. 6B described above, it is possible to reduce the necessity to consider the orientation of the suture 16 when the suture 16 is brought to face the holding portions 42a and 42b.

The second end (end face) 34 of the securing portion 14 does not have to be substantially rectangular. For example, the second end (end face) 34 of the securing portion 14 may be circular, as shown in FIG. 16C, or elliptical. In this case, the holding portions 42a and 42b may or may not be orthogonal to each other.

In the above-described example, an example in which the securing portion 14 is one integral unit has been described. In the following, an example in which the securing portion 14 is formed of a plurality of materials will be described.

Figure 23A:
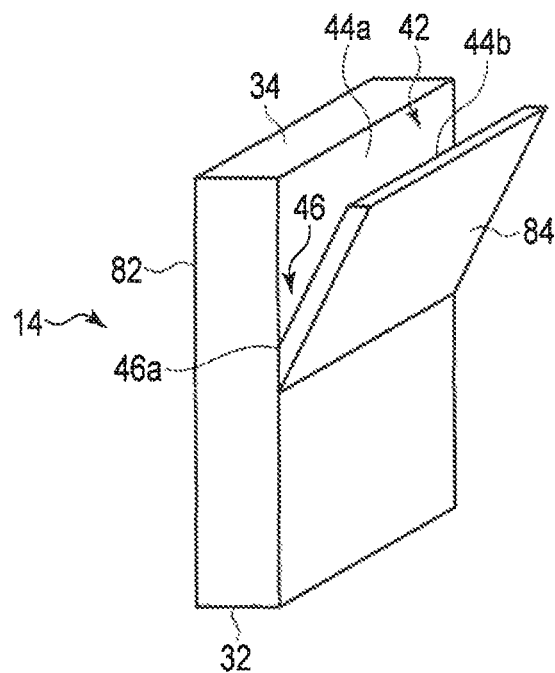
FIG. 23A is a schematic perspective view showing a state in which a securing portion is formed of two bodies of a rigid body and an elastic body, and the rigid body and the elastic body cooperate to form a holding portion to hold a suture, different from the securing portion of the suture securing instrument shown in FIGS. 1A to 1E.

As shown in FIG. 23A, the securing portion 14 includes a block-like or columnar rigid body 82, and an elastic body 84 which is supported by the rigid body 82 and much more elastically deformed as compared with the rigid body 82.

The rigid body 82 is formed in an appropriate columnar shape such as, for example, a polygonal columnar shape, a semi-cylindrical shape, car a semi-elliptical columnar shape. The part where the elastic body 84 is supported by the rigid body 82 forms a holding portion 42 for locking and holding the suture 16 by cooperation between the rigid body 82 and the elastic body 84. Therefore, the part is formed into a shape that can maximize a contact area that contacts the suture 16. Accordingly, it is preferable that the part where the elastic body 84 is supported by the rigid body 82 be a plane, or a convex or concave curved surface.

The elastic body 84 is supported by the rigid body 82 at a position close to the first end 32 and is separated from the rigid body 82 at a position close to the second end 34.

Figure 23B:
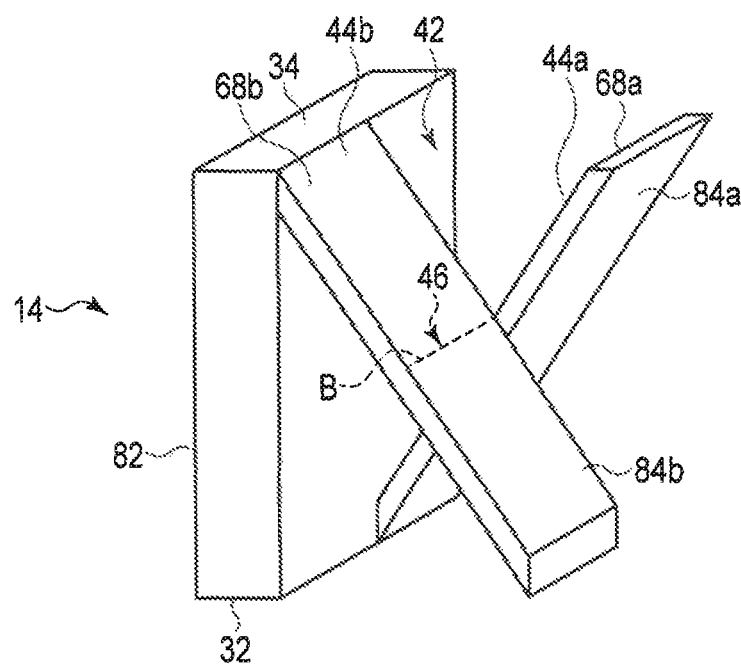
FIG. 23B is a schematic perspective view showing a modification of the securing portion of the suture securing instrument shown in FIG. 23A, in which the securing portion is formed of three bodies of a rigid body and two elastic bodies, and the two elastic bodies form a holding portion to hold a suture.

In the example shown in FIG. 23B, the securing portion 14 includes a block-like or columnar rigid body 82, and two elastic bodies 84a and 84b which are supported by the rigid body 82 and are much more elastically deformed as compared with the rigid body 82. That is, the securing portion 14 shown in FIG. 23B is formed of three bodies.

The elastic body 84*a* is supported by the rigid body 82 at a position close to the first end 32 and is separated from the rigid body 82 at a position close to the second end 34. The elastic body 84*b* is supported by the rigid body 82 at a position close to the first end 34 and is separated from the rigid body 82 at a position close to the second end 32. As in the example shown in FIGS. 21A to 21D, the suture 16 (not shown) is placed at a position shown by a broken line B orthogonal to the inclination direction of the two inclined surfaces 68*a* and 68*b*. At this time, the position indicated by the broken line B is used as the bottom portion 46 of the holding portion 42. Furthermore, of the inclined surfaces 68*a* and 68*b*, portions farther from the position indicated by the broken line B than the first end 32 are used as the guides 44*a* and 44*b* of the holding portion 42. In this example, the guides 44*a* and 44*b* are in a non-facing position, where they do not face each other.

The two elastic bodies 84*a* and 84*b* may be in contact with each other, or may be spaced apart as in the example shown in FIG. 21C.

Figure 23C:
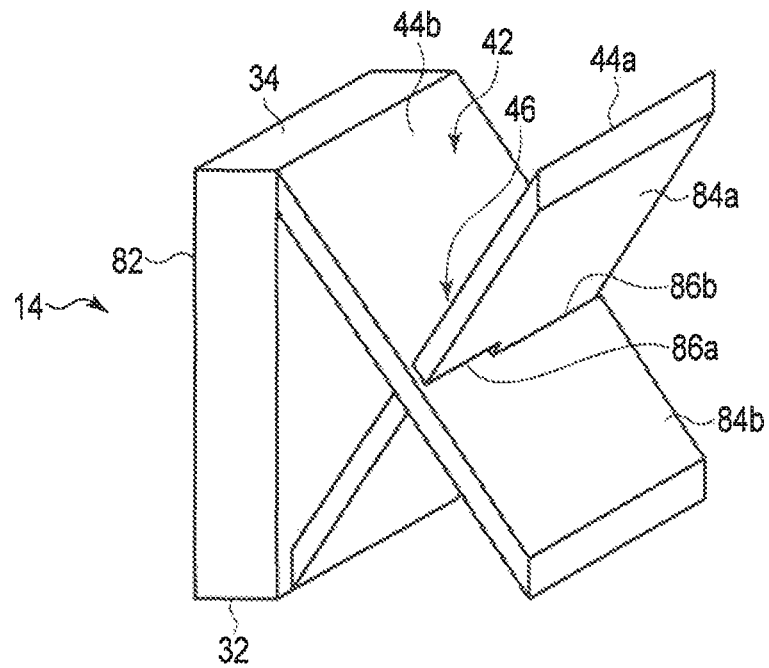
FIG. 23C is a schematic perspective view showing a modification of the securing portion of the suture securing instrument shown in FIG. 23B, in which the securing portion is formed of three bodies of a rigid body and two elastic bodies fitted each other, and the two fitted elastic bodies form a holding portion to hold a suture.

In the example shown in FIG. 23C, the securing portion 14 includes a block-like or columnar rigid body 82, and two elastic bodies 84*a* and 84*b* which are supported by the rigid body 82 and are much more elastically deformed as compared with the rigid body 82. That is, the securing portion 14 shown in FIG. 23C is formed of three bodies similarly to the example shown in FIG. 23B.

The elastic body 84*a* is supported by the rigid body 82 at a position close to the end 32 and separated from the rigid body 82 at a position close to the second end 34. The elastic body 84*b* is supported by the rigid body 82 at a position close to the first end 34 and separated from the rigid body 82 at a position close to the second end 32. The elastic body 84*a* includes a substantially U-shaped recess 86*a*. The elastic body 84*b* includes a substantially U-shaped recess 86*b*. The elastic bodies 84*a* and 84*b* are fitted in each other's recesses 86*a* and 86*b*. The elastic bodies 84*a* and 84*b* form a bottom portion 46 among the guides 44*a* and 44*b* and the recesses 86*a* and 86*b*; that is, a holding portion 42 in which the suture 16 is locked and held is formed. In this example, the guides 44*a* and 44*b* are in a facing position, where they face each other.

As described above, the securing portion 14 may have various shapes in which the suture 16 can be guided to the holding portion 42. The cylindrical body 12 may have any shape that allows the inner circumferential surface 26 to cooperate with the securing portion 14 to secure the suture 16 to the securing portion 14 in a locked and/or secured state.

The securing portion 14 shown in FIGS. 20 to 23C is used together with the appropriate cylindrical body 12 and the appropriate suture 16 to form the suture securing instrument 10. At this time, the suture securing instrument 10 can secure the suture 16 with a stable securing force.

In the examples mentioned above, the groove 26*a* is formed in the inner circumferential surface 26 of the cylindrical body 12.

Figure 24A:
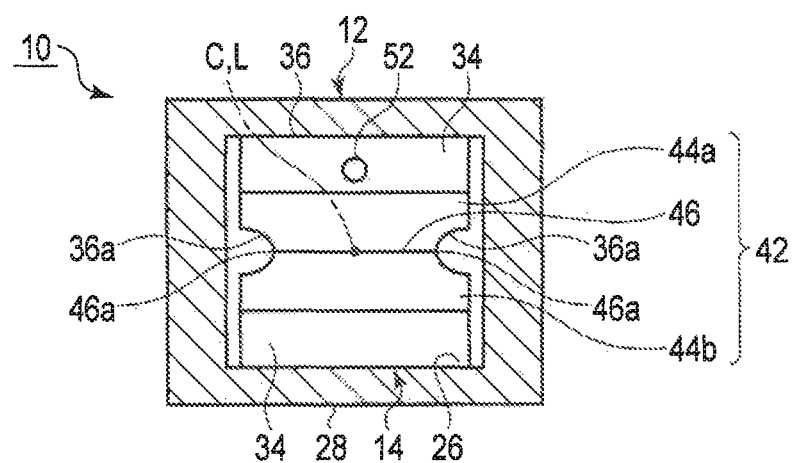
FIG. 24A is a schematic view showing a cross section of a cylindrical body with no groove in which a suture is placed and a securing portion with a groove in which a suture is placed, different from the external shape of the cylindrical body and the securing portion of the suture securing instrument shown in FIG. 1C.
Figure 24B:
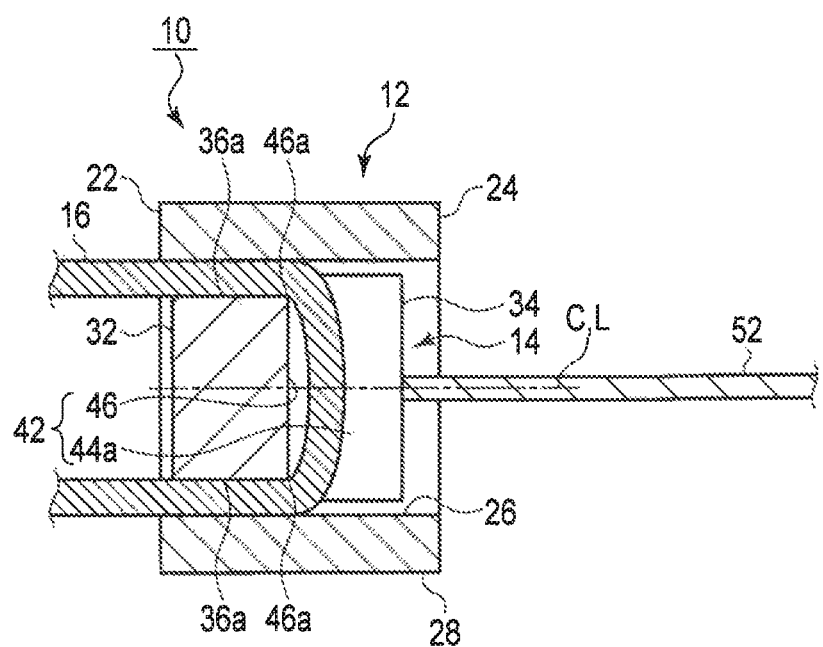
FIG. 24B a schematic cross-sectional view of the suture securing instrument shown in FIG. 24A at the same position as the position taken along line 5B-5B in FIG. 5A.

In the example shown in FIGS. 24A and 24B, the securing portion 14 includes a pair of concave grooves (suture locking grooves) 36*a* the outer circumferential surface 36 continuous with the pair of end portions 46*a* of the bottom portion 46 of the holding portion 42. The concave grooves 36*a* are preferably continuous from the bottom portion 46 of the holding portion 42 to the first end 32 of the securing portion 14.

On the other hand, no concave groove 26*a* is formed in the inner circumferential surface 26 of the cylindrical body 12.

As described above, the suture 16 may be locked and/or held b n the inner circumferential surface 26 of the cylindrical body 12 and the outer circumferential surface 36 of the securing portion 14.

In the example shown in FIG. 1D described above, the concave grooves 26*a* are formed in the inner circumferential surface 26 of the cylindrical body 12, and in the example shown in FIG. 24A, the concave grooves 36*a* are formed in the outer circumferential surface 36 of the securing portion 14 did. As a matter of course, it is preferable that the concave grooves 26*a* are formed in the inner circumferential surface 26 of the cylindrical body 12 and the concave grooves 36*a* are formed in the outer circumferential surface 36 of the securing portion 14. For this reason, the concave grooves 26*a* and 36*a* are formed in at least one of the cylindrical body 12 and the securing portion 14.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A suture securing instrument that secures a suture, comprising:
    a cylindrical body including an inner circumferential surface extending along a longitudinal axis; and
    a securing portion extending along the longitudinal axis and configured to secure the suture, the securing portion including:
        a first end and a second end;
        an outer circumferential surface supported by the inner circumferential surface of the cylindrical body, the outer circumferential surface of the securing portion being configured to move along the longitudinal axis relative to the cylindrical body; and
        a holding portion configured to hold the suture, when it is interposed between the cylindrical body and the securing portion, wherein:
            the holding portion includes a groove having a bottom portion configured to lock the suture at the second end such that the suture intersects the longitudinal axis; and
            when the suture is held on an end face of the second end, the suture bends such that the suture is held on the outer circumferential surface of the securing portion, and the securing portion is fitted in the cylindrical body in the direction of the longitudinal axis.

2. The suture securing instrument according to claim 1, wherein the securing portion is configured to apply tension to the suture in the holding portion in cooperation with the cylindrical body while holding the suture in the holding portion.

3. The suture securing instrument according to claim 1, wherein the holding portion includes a pair of guides configured to guide the suture.

4. The suture securing instrument according to claim 3, wherein:
    the bottom portion is substantially V-shaped and is continuous to the guide.

5. The suture securing instrument according to claim 3, wherein the pair of guides comprises a first guide and a second guide and the pair of guides are in a non-facing position such that the first guide does not face the second guide.

6. The suture securing instrument according to claim 1, wherein the inner circumferential surface of the cylindrical body and the outer circumferential surface of the securing portion are separated, while the suture is being held.

7. The suture securing instrument according to claim 1, comprising a concave groove that is provided in at least one of the inner circumferential surface of the cylindrical body or the outer circumferential surface of the securing portion, wherein the concave groove is configured to hold the suture between the inner circumferential surface of the cylindrical body and the outer circumferential surface of the securing portion.

8. The suture securing instrument according to claim 1, wherein the securing portion is press-fitted and supported in the inner circumferential surface of the cylindrical body.

9. The suture securing instrument according to claim 1, wherein the securing portion is engaged with and supported by the inner circumferential surface of the cylindrical body.

10. The suture securing instrument according to claim 1, comprising a wire that is connected to the securing portion, that is inserted into the cylindrical body, and that is pulled to the cylindrical body, to support the outer circumferential surface of the securing portion to the inner circumferential surface of the cylindrical body.

11. The suture securing instrument according to claim 10, wherein the wire includes a breakable portion to be broken by a tension applied to the wire after the securing portion is supported by the cylindrical body and the suture is secured to the suture securing instrument.

12. The suture securing instrument according to claim 10, wherein the wire is cut at an appropriate position.

13. The suture securing instrument according to claim 10, further comprising an applicator that includes:
   a sheath through which the wire is inserted;
   an operation portion disposed on a proximal end side of the sheath to axially move the wire relative to the sheath;
   the applicator being configured to move the securing portion relative to the cylindrical body.

14. The suture securing instrument according to claim 13, further comprising a cutting mechanism provided in at least one of the cylindrical body and the applicator and configured to cut the wire.

15. The suture securing instrument according to claim 10, further comprising a cutting mechanism provided in the cylindrical body and configured to cut the wire.

* * * * *